United States Patent
Solomon

(10) Patent No.: US 8,623,638 B2
(45) Date of Patent: *Jan. 7, 2014

(54) INTELLIGENT MULTIFUNCTIONAL MEDICAL DEVICE APPARATUS AND COMPONENTS

(76) Inventor: Neal Solomon, Oakland, CA (US)

(*) Notice: Subject to any disclaimer, the term of this patent is extended or adjusted under 35 U.S.C. 154(b) by 903 days.

This patent is subject to a terminal disclaimer.

(21) Appl. No.: 12/462,787

(22) Filed: Aug. 7, 2009

(65) Prior Publication Data

US 2010/0068798 A1 Mar. 18, 2010

Related U.S. Application Data

(60) Provisional application No. 61/188,384, filed on Aug. 8, 2008.

(51) Int. Cl.
*C12M 1/34* (2006.01)
*G01N 33/48* (2006.01)
*G06N 5/02* (2006.01)

(52) U.S. Cl.
USPC .............. 435/287.2; 435/287.1; 422/68.1; 702/19; 702/20; 706/46; 604/890.1

(58) Field of Classification Search
USPC .............. 604/890.1; 702/19, 20; 422/68.1; 706/46; 435/287.1, 287.2
See application file for complete search history.

(56) References Cited

U.S. PATENT DOCUMENTS

| | | | |
|---|---|---|---|
| 2003/0140317 A1* | 7/2003 | Brewer et al. | 716/1 |
| 2004/0147906 A1* | 7/2004 | Voyiazis et al. | 604/891.1 |
| 2005/0043894 A1* | 2/2005 | Fernandez | 702/19 |

* cited by examiner

*Primary Examiner* — William H Beisner
*Assistant Examiner* — Danielle Henkel

(57) ABSTRACT

The multifunctional medical device contains system on chip (SoC) computation functionality to organize several functional modules consisting of analytical, diagnostic and therapeutic tasks in the microfluidic assembly. Micro-valves, micro-tubes, micro-wires and gates organize the chambers of the flexible modules which hold multiple chemical and biological agents for combination on demand.

18 Claims, 32 Drawing Sheets

Phase I

Phase II

Phase III

INTELLIGENT MULTIFUNCTIONAL MEDICAL DEVICE APPARATUS AND COMPONENTS

CROSS-REFERENCES TO RELATED APPLICATIONS

The present application claims the benefit of priority under 35 U.S.C. §119 from U.S. Provisional Patent Application Ser. No. 61/188,384, filed on Aug. 8, 2008, the disclosure of which is hereby incorporated by reference in their entirety for all purposes.

FIELD OF THE INVENTION

The invention involves micro electro mechanical systems (MEMS) applied to medical devices and components. The components include semiconductor devices, sensors, microfluidic devices and microarrays. The present system includes devices and components for micro total analysis systems (μTAS) and lab on a chip (LOC) apparatuses. The invention applies to diagnostic and therapeutic aspects of medical intervention.

BACKGROUND

As scientists discover the mechanics of genetic processes, our understanding of the sources of diseases increases. The benefits of understanding genetic dynamics and proteomics regulatory processes assists in development of a new generation of medical devices able to diagnose, regulate, manage and cure complex diseases. The potential exists to develop personalized drug therapies to target specific genetic pathologies.

Regarding diagnostic systems, MEMS is an umbrella for a class of new medical devices able to identify genetic mutations and proteomic dysfunctions. While largely external in vitro devices, DNA microarrays, RNA microarrays and protein microarrays provide feedback to identify an individual's genetic information. Protein microarrays use antibodies to assess protein functional responses. In addition, whole cell assays test cells with analytes to assess specific responses to chemical inputs. Multi-phenotype cellular arrays are used for bio-sensing of specific inputs in order to study cell functions.

Though DNA, RNA, protein and whole cell arrays have developed separately, a new generation of lab on chip (LOC) and micro-total analysis systems (μTAS) technologies have emerged as well that integrate several functions in a single device. These multi-purpose arrays provide clinical diagnostic data to practitioners.

In addition to these external devices, the evolution of radiological diagnostic tools has provided a revolution to analytical practitioners. In particular, the use of CT, PET and MRI technologies provides detailed data on specific disease progression. In addition to these external radiological diagnostic technologies, the internal sensing "pill" camera records and transmits digital images to substitute for the surgical intervention of exploratory surgery. Finally, the use of implanted sensors assists in the regulation of simple deterministic expert systems.

The convergence of nanotechnology with biology has produced "bionano" devices. In the main, the use of nanotechnology is limited to particles that are targeted to specific tissue in order to identify pathology and, when combined with directed radiation, provide a therapeutic alternative. The advent of self-assembled peptide nano-biomaterials provides interesting opportunities for diagnostics and therapeutics. The use of nano-scale devices, in which collective behaviors are controlled for therapeutic as well as diagnostic modes, provides an advancement of the bionano field.

Regarding therapeutic medical devices and systems, the field has evolved from the development of the hearing aid and the cardiac pace maker. For instance, the implantable brain pacemaker has been developed to regulate epileptic energy pulses and blood glucose monitoring is regulated with an insulin pump. Moreover, implantable pain management devices are used to control chronic pain. Microfluidic devices to target drug delivery, primarily using a deterministic expert system control model, have also been developed. All of these devices are simple single-function mechanisms targeted to a specific disease or disorder.

An emerging scientific field is providing a new set of technologies from bio-inspired computing. Complexity science deals with self-organizing systems that learn in indeterministic environments. The inspiration from the autonomic nervous system and the human immune system provide computing systems that emulate these complex biological processes. Autonomic computing self-diagnoses, self-heals and self-regulates distributed networks. The human immune system provides inspiration for immunocomputing models that emulate protein regulatory network behaviors in order to solve complex optimization problems. Swarm intelligence metaheuristics provides solutions to optimization problems as well. For instance, the ant colony optimization (ACO) metaheuristic provides a model to solve network computing problems. These models share the ability to develop solutions to problems in self-organizing systems, including plasticity behaviors, in indeterministic environments. In effect, these complex computing and control systems learn. So far, these complex computing models have not been applied to medical devices.

The ability to use genetic and proteomic information to solve complex pathologies provides a new generation of opportunities to build medical devices that are customized to each individual's specific disease(s). Our understanding of cancer, for instance, as the combination of multiple genetic mutations, suggests that each disease type is classed into a typology that can be solved with specific targeted therapies. Given this new knowledge, it is logical to build medical devices that are personalized to specific diseases of each individual. In particular, the use of medical devices focused on solving problems involving pathologies associated with cardiovascular, neurological, immunological and endocrinological systems, and with cancer, is a next step.

Each of the prior medical devices has limitations. For the most part, none of the implantable medical devices are "intelligent". Rather, they are simple deterministic systems. They are also single function devices focused on a specific narrow medical problem. Because they are merely deterministic expert systems, they do not combine diagnostic and therapeutic functionality. In the diagnostic mode, they do not provide sophisticated modeling functions. Further, prior MDs are not networked since they typically involve a single device performing a single function. Finally, these devices are not useful in personalized medicine, which require complex analysis and targeting of individual therapies to unique problem sets.

What is needed? We need active intelligent medical devices that are able to work with other medical devices to solve multiple medical problems. We need complex medical devices that are capable of integrating diagnostics and therapeutics in order to maximize efficiency, to promote early detection and treatment and to modify functionality with feedback mechanisms to solve complex biological optimization problems in biological regulatory networks. The present system develops an intelligent multifunctional medical device system.

PROBLEMS THAT THE SYSTEM SOLVES

The present system solves a range of problems. How can we develop an intelligent medical device (iMD) that coordinates diagnosis and therapy? How can the iMD coordinate sensors and integrated circuits? How is the processing of chemical and biological fluids administered by using the iMD? How is the implantable iMD coordinated with external computation and modeling? How does the device collect samples and data in real time? How does one integrate multi-functionality into an efficient iMD design? How is the implantable device installed with minimal invasiveness? How are nano-components integrated into the iMD? How does the iMD use sensors and probes for maximum effect? How does the iMD efficiently analyze biological data? How are solutions to complex problems developed and refined in the iMD? How is drug delivery optimized in the iMD? How can we construct customized drugs for therapies to individual patient pathologies? How can an iMD self-organize and adapt to indeterministic environmental conditions? How can multiple iMDs be coordinated, particularly for multiple applications? Solving these problems presents opportunities to develop a new generation of highly effective medical devices.

SUMMARY OF THE INVENTION

The present invention describes the integration of several iMD components involving computation, lab-on-a-chip (LOC) and microfluidic elements of diagnostic and therapeutic modules. The functional components of the iMD consists of a data collection module, a diagnostic module and a therapeutic module. The functional organization of these modules includes the storage, integration, analysis and reaggregation of chemical and biological substances.

While a system on a chip (SoC) computing device controls the overall iMD, each module is controlled by a separate ASIC or FPGA to manage specific apparatus functional operations. The on-board computing systems are integrated with external computation resources for substantial analytical and management functionality.

Multi-attribute microarrays are used in the diagnostic module to assess and analyze biological samples in order to solve pathology optimization problems. A network of LOC chambers and compartments, which transform on-demand, allow the combination of customized chemical and biological entities. The LOC compartments transform their functional geometries with moveable gates and partitions to accommodate specific procedures. The diagnostic and therapeutic modules have access to external iMD satellites and reservoirs for refilling and evacuating chemicals.

The iMD is fabricated using similar techniques to the semiconductor fabrication industry. Each layer of the device modules is built like a multi-layer (3D) integrated circuit. While there is a parallel in the comparison between the fabrication technologies of the iMD and the chip, particularly involving the electrical interconnects, the iMD varies because of the use of microfluidic channels. These channels require specialized techniques to manufacture.

Novelties

Some of the novelties of the present iMD are drawn from literatures of semiconductors, robotics and nanotechnology. Because iMDs are complex devices with multiple integrated components, they share some interesting elements with integrated circuits. However, where they differ markedly is in the requirement to manage fluidic elements. One may conceive of an iMD as a highly complex system on a chip (SoC) with multiple components. This view provides insight into the iMD fabrication process as well, which share some characteristics of chip manufacture.

An iMD is a micro-robotic device that resembles a Mars lunar rover because of the requirement to collect data, analyze the data and provide external therapeutic functionality. Because of this insight, robotics is a useful application, particularly since devices reconfigure internal components in response to external stimulus. Specifically, iMDs are a special class of evolvable hardware (EHW). EHW has been applied to FPGAs and to collectives of nanorobotics, but not to iMDs.

iMDs are smart adaptive systems that are modular, flexible, integrated and customized.

ADVANTAGES OF THE INVENTION

There are a number of advantages of the present invention. Analyses of biomedical problems are performed by the iMDs for rapid, efficient, precise and on-demand response. The system automatically assesses biomarkers and responds to the underlying disease. The system is able to develop customized solutions within resource constraints. The system develops personalized medicine targeted to specific pathologies, which allows the management of pathologies over time. The invention allows for the simultaneous diagnosis of multiple attributes, which allows for the analysis of multiple factors. The present invention is also pro-active since iMDs anticipate pathology developmental phases and act to prevent disease degradation.

Procedures that once required hospital surgical intervention at substantial cost and risk may now be performed automatically by an iMD and installed and serviced in a physician's office, which dramatically cuts costs. Because they are modular, the iMDs may be periodically serviced by a physician rather than undergoing major surgery.

DESCRIPTION OF THE INVENTION

(I) Computation in the iMD

An iMD requires an embedded controller to manage its component parts. While application specific integrated circuits (ASICs) will manage a specific component that performs a deterministic functionality, the system also uses field programmable gate arrays (FPGAs) and system on chip (SoC) technologies to maximize multi-functionality. Memory components provide supplemental memory capacity to the logic components. In addition to internal computing devices, the system also works cooperatively with external computer resources.

(1) System for ASIC Component of iMD for Single Function Control

Application specific integrated circuits (ASICs) are semiconductors that perform specific logic functions. ASICs are used in the iMD to manage simple processes of activating a function. By accessing sensor inputs, ASICs activate the specific task of opening and closing a partition, gate, a valve, a regulator or a filter. ASICs also perform functions of moving sensor data to memory and sending out and receiving probes. ASICs appear on each layer of the iMD modules, each of which deals with a different functionality. ASICs are pre-programmed and have deterministic logic functionality.

ASICs are connected to the central embedded controller (typically an SoC) that manages and regulates the overall iMD processes. However, the ASICs are able to operate independently in response to specific local behaviors.

A typical iMD has several ASICs. The SoC coordinates the timing of operation of the ASICs in the iMD. This is done by modulating the sensor data that is input to the ASICs. Though multiple ASICs operate simultaneously, the SoC coordinates their behaviors when conflicts arise by blocking or delaying the timing of activation in a sequence of ASIC functions.

The analogy of multiple ASIC operations is in a camera. An ASIC processes the digital sensor data by forwarding the data to memory. Other ASICs perform other functions in the camera in a sequence of operations controlled by a microprocessor.

(2) System for FPGA Component of iMD for Rapid Prototyping

Field programmable gate arrays (FPGAs) are complex programmable logic devices that move from one ASIC position to another position. Deterministic FPGAs have pre-programmed logic, while indeterministic FPGAs are programmable. Indeterministic continuously programmable FPGAs (CP-FPGAs) are used for rapid prototyping in industrial engineering projects.

IMDs use FPGAs to perform specific logic functions beyond the capabilities of ASICs. These functions include the regulation of microfluidic flow control, assessment of diagnostic data, control and regulation of drug combinations, simultaneous coordination of two or more functions and so on. In these examples, complex behaviors oscillate from one specific position to another without deterministic certainty.

In those cases in which restructuring of the architecture of the iMD or its components is required, FPGAs are more suitable to perform complex functions rapidly than ASICs. ASICs work with FPGAs to coordinate and synchronize functions.

While FPGAs are used in indeterministic environments by oscillating from one ASIC position to another, they are also useful in deterministic environments. In these cases, they are more efficient than using multiple ASICs.

FPGAs receive signals from sensors and actuators in order to organize and coordinate programming functionality. However, in their indeterministic mode, the FPGAs produce a novel sequence of ASIC structures to solve a complex optimization problem within time constraints.

The operations of multiple FPGAs are coordinated by the embedded SoC controller. When one FPGA is off-line during the restructuring process, the other FPGAs are operational. FPGAs are useful for controlling data collection, internal operations, diagnostics and therapeutic behaviors of the iMD.

The reconfiguration processes of FPGAs are synchronized with the restructuring capacities of iMD hardware. This coordinated reconfiguration of hardware processes constitutes self-organization operations that allow the iMD to change its architecture to evolving environmental conditions.

(3) System for SoC iMD Embedded Controller

System on chip (SoC) technology consists of a semiconductor that integrates multiple logic and memory components into a single device. SoCs are typically multi-core hybridized devices that include microprocessor and memory components and may include FPGAs. Advanced SoCs consist of multiple layers, like a multi-story building, with different functionality on each layer.

An SoC is the main controller for the iMD. Located in a central layer of the iMD, the SoC manages and regulates all of the functions of the device, including peripheral FPGA and ASIC component controllers. Because it has multiple logic cores, whether microprocessor or FPGA, the SoC performs multiple functions simultaneously, including collection, organization and analysis of data, selection, synthesis, administration and regulation of chemicals and the coordination of operations within the device.

Because it uses microprocessors, the SoC stores data in and retrieves data from separate memory modules and databases. The memory components are optimized for each specific logic device. Therefore, there are multiple types of memories (DRAM, SRAM, etc.) employed to match and optimize several different kinds of logic devices. Specific databases store and access data in specialized libraries for each particular kind of iMD problem, thereby maximizing efficiency.

In general, the use of microprocessors involves deterministic programming for use in complex expert systems for the control of the main diagnostic and therapeutic iMD functions. However, when in combination with FPGAs, the SoC programming is also indeterministic and thus able to solve complex multi-objective optimization problems by employing the feedback mechanisms of the iMD in real time. When used in conjunction with metaheuristics, the SoC is an adaptive logic device that is capable of learning, self-organization and plasticity behaviors.

The SoC is critical for analytical capabilities of the iMD. The SoC is used to model specific problems on site in real time in order to regulate the flow of chemicals in the iMD and to interact with its biomedical environment. In addition, the SoC controls the peripheral medical devices of nano-probes, micro-probes, micro-sensors, nano-cargo delivery devices and micro-cargo delivery devices.

The SoC connects to the layers of the iMD by a network of interconnects along the edge of each layer. Each layer has separate logic devices that connect to the SoC. The SoC is powered by the battery layer of the iMD.

The SoC interacts with external computation resources. In order to supplement its own capabilities, including modeling and analytical functions, the SoC engages external computation capabilities. As the central embedded controller of the iMD, the SoC also receives program code remotely from external computer sources at regular intervals to update its software.

(4) System for External Computation for iMD

Because of the limitations of internal iMD computation, the system accesses substantial external computation resources. These external computers are used for analysis of complex data sets, modeling of optimization problems, analysis and development of solutions and monitoring of the iMD. Because of the use of external computer capabilities, the system is able to accelerate on-board iMD analytical functions. In one useful application of the external computer capabilities, the iMD is able to more rapidly perform multiple simultaneous functions while the external computer system performs analyses integrating data from therapeutic feedback.

In addition to supplemental analytical functions, the use of external computation resources provides monitoring and updating of iMD software programming. However, one limitation of this mode of interaction is the time lags that occur in accessing external computer systems. This limitation is minimized with scheduling protocols and implementation of queuing procedures for seamless analytical operations. Specifically, the system is designed to employ the on-board SoC while using the external computer system to perform less time sensitive analytical procedures. Also, the system uses fuzzy logic algorithms to solve problems rapidly to a specific degree that falls short of a complete solution that would require far more massive computer resources.

The use of external computation allows the system to employ vast memory storage capabilities. The iMD itself maintains efficient memory management processes, but is constrained by computational limitations. When it uses external computer capabilities, however, the system is not restricted; the iMD accesses substantial memory and database functionality, including numerous specialized biological libraries. The iMD stores and backs-up much of its memory off-site as a failsafe mechanism.

The computing system uses security protocols to prevent unauthorized access.

(5) System for iMD Communications Components

The iMD has two main communication modes: wire and wireless. In its wired communication mode, the system uses a transmitter and receiver to access data signals. In its wireless mode, the iMD uses an antennae to transmit and receive data. The iMD communicates with other iMDs and with other internal components as well as with external computer resources. In its external communication mode, the system focuses on broadcasting data with wireless communications at significant range. External computers broadcast to multiple iMDs.

IMDs communicate with other iMDs using a broadcast wireless mode as well as direct wired contacts. Each iMD communicates with probes and micro-devices by using nano-wire functionality. In most cases, the iMD's default to the wired communication mode for internal communication.

The communication components are located adjacent to the computer layer of each iMD to maximize efficiency.

(II) Lab on Chip Components (6) System for Multi-Attribute Microarrays in an iMD Microarrays, or biochips, are passive external MEMS devices that test specific bio-molecules, including DNA, RNA, protein, antibodies and whole cells, for specific biochemical properties. DNA microarrays have rows of wells to test for specific single nucleotide polymorphisms (SNPs) or gene mutations. Microarrays combine semiconductor fabrication lithographic technology with biochemistry to test for specific chemistries. Micro total analysis systems (µTAS) combine multiple analytical microarray components in layers in a single device to simultaneously test for different types of bio-molecules.

The present system uses a µTAS component on a specific module of the iMD. The µTAS uses analytes for on-site testing of limited bio-chemical categories primarily to confirm therapeutic feedback of the system. The multilayer µTAS is enclosed in a modular package as a specific modular layer of the iMD. A motorized hinge lifts and closes a flap to allow specific fluids to flow into the µTAS component. If DNA is analyzed, DNA polymerase is used to amplify the DNA sample. The biological fluid is then evenly spread onto the top plane of the µTAS by the closed-position flap and leveled into the top layer wells. Excess fluid is poured to the other layers of the µTAS. An analyte is pumped into the system from an adjacent chamber through micro-channels. The system then measures and analyzes the reaction of the bio-chemicals to the analyte. In a final phase of the process, the fluid is cleared by draining the device plane and flushing with a neutral fluid. The internal µTAS module is particularly useful for biomarker detection in the whole cell part of the microarray in order to assess the usefulness of a particular drug combination therapy.

In another embodiment of the µTAS, a single plane is used, but specific wells contain four distinct partitions. A movable screen is employed over the surface to allow only one of the four wells to be filled at a time. As the screen moves, another well in each set is accessible for a different type of biochemical until the four wells are filled. This model is useful for testing DNA, RNA, protein and whole cells in sequence in an efficient assembly. In this model, each chamber is tested with a different analyte. This model is similar to the different colors of pixels used in a CMOS digital sensor which share a common pixel well.

Fluidic chambers are accessed on the periphery of the µTAS module to store chemicals, antibodies and analytes for testing procedures. The microfluidic reactions are assessed and recorded by an FPGA integrated in the module layer of the iMD. Unitary chambers store different chemicals and biological fluids, which are connected in rows on the periphery of the main µTAS chamber. Micro fluidic channels are used to transport the chemicals and biological fluids to and from the microarray device. The micro-pump applies pressure to move the fluids through the micro-channel network.

(7) Apparatus for an Integrated LOC in an iMD

The iMD uses data obtained about an individual from external microarray analyses as well as from the µTAS. Because massive datasets are available by analyzing biological data using microarrays—including DNA, SNPs and protein mutations—it is useful to coordinate these datasets with iMD functionality. Data from µTAS are input into an external computer for analyses. The data is then modeled and input into the iMD. This data is useful in order to identify specific genetic mutations and dysfunctional proteins as well as dysfunctional protein regulatory networks that are the source of pathologies. The external computer system maintains large gene libraries that are used to compare an individual's unique genetic condition. Once these specific customized pathologies are identified, the iMD efficiently focuses on identifying and analyzing these specific genes and proteins.

(III) Integrated LOC Components (8) System for Valves and Tubes for Internal 3D iMD Plumbing While each layer of the iMD contains microfluidic conduits connecting the chemical holding chambers, the iMD also contains tubing connecting the modular network iMD components—such as sensors and probes—creating an internal plumbing network. The tubes are connected to valves and joints at the edges of each layer. The tubes and conduits are flushed with fluids by using the pressure and vacuum properties of the micro-pump mechanism.

The internal tubing architecture is analogized to electronic semiconductor interconnects, while the conduits are analogized to multilayer semiconductor vias.

Because they are three dimensional micro-devices, the iMD tubing and conduits interconnect the fluidic components both within each modules' layers and between the modules. The tubing has caps at each end, which are removed when attaching to a new component. The tubing is used not only to transport chemicals but also for probes and nano-devices.

A system of valves at key locations is used to connect the tubes at specific junctions. In effect, the valves behave as three dimensional gates by opening and closing to allow fluid to move through particular joints.

(9) System for Electrical Components for 3D iMD

Micro-scale and nano-scale wires are used to connect electrical components within the iMD. Within each module, the nano-wires are integrated into each layer at the edges and seams. Electrical vias connect each adjacent layer as well as non-adjacent layers to each other. Further, inter-module vias are used to connect the modules themselves.

Electrical interconnects are critical for connecting the computing components of the system. The interconnect system behaves as a web of wires connecting to the computing devices. The interconnect system connects the computing devices to each other, to the sensor system and to the specific functional components in the iMD system.

Like the tubing provides the iMD a plumbing system, the internal wiring provides the iMD an internal integrated electrical system.

(10) Micro-Pump Apparatus for iMD

The system uses a micro pump array to activate the fluidic control processes of the iMD. Micro pumps are located in the diagnostic and therapeutic modules of the iMD. In one case, a micro pump is located in the center of a module in order to create suction pressure at one end and vacuum pressure at the other. In another embodiment, two micro pumps work in concert on the same layer, one pushing and the other pulling. This model is useful in order to push fluid from the module on one side with one pump while the other pump is used to pull fluid into the module from another point.

Since both the diagnostic and therapeutic modules use probes and nano-devices to collect data or target specific tissues at precise external locations, the pumping mechanism is critical to provide control of the auxiliary devices.

(IV) 3D iMD Architecture

(11) System for Chambers, Channels and Vias in 3D iMDs

The integrated iMD consists of multiple functional layered modules. While each iMD consists of different modules, one typical configuration consists of an analytical module, a diagnostic module, a therapeutic module and a power supply. The analytical module consists of the computation logic and memory components. The diagnostic module includes the μTAS components as well as chambers for probes and nano-devices. The therapeutic module consists of a storage mechanism for a combination of chemicals as well as nano-devices for their targeted delivery.

IMDs may be integrated with multiple therapeutic and diagnostic components. Further, a systems approach integrates multiple iMDs into a network. The full system includes iMDs and external computation resources.

Each layer consists of a complex network of integrated cavities, chambers, conduits, channels and vias for the transport of fluids for specific functionality. Since the μTAS components of the diagnostic layer require fluid interaction processes, the diagnostic module contains chambers for fluids as well as the network of micro-fluidic tubing and conduits. The therapeutic layer requires reservoirs of fluids as well as the network of micro-fluidic tubing and conduits. The precise architecture settings of each layer and of each module varies depending on the specific functionality and the specific targeted pathology and therapeutic procedure.

The LOC contains several layers of distinct compartments for storing chemicals and biologicals. A layer of compartments is organized for traditional drugs, while another layer is organized for customized drugs, agents and proteins. An additional layer of compartments is organized for antibodies, stem cells, cell samples, DNA and RNA samples and nano- and micro-robot collectives. Other layers are available for mixing the various chemicals and biologicals on demand for specific customized therapies. Further layers are provided for evacuating chemicals and biologicals.

(12) System for Gates and Movable Joints in 3D iMD

Movable gates are used to open and close specific conduits in the iMD. The gates use a flexible joint that is activated by the computer controller. Gates are used on a specific layer of a module to perform a function such as allowing fluid to pass or damming fluid at a particular point.

The gates behave as movable reservoir partitions that permit and restrict the flow of fluid at key locations.

(V) 3D iMD Functionality

Transforming Geometries

(13) Method for Switching Mechanism to Restructure Geometries of Layers of 3D iMD While the 3D iMD structure consists of interconnected functional modules, its functionality consists of restructuring the layers of each module to activate specific utility. Much like an FPGA restructures from one ASIC position to another in order to maintain multi-functionality, the 3D iMD has a switching mechanism that restructures its layers.

The analogy of the switching mechanism of the 3D iMD is to the changing configurations of a house as its rooms are reconfigured with shifting positions of partitions. In this approach, for instance, a large reservoir chamber is partitioned in order to segregate a set of multiple specific chemicals. As it uses its reservoir capacity, the iMD may restructure the main chamber to maximize utility, particularly as its mission changes.

(14) Method for Periodic Switching and Shifting Partitions in 3D iMD

The system automatically restructures its component architectures at specific thresholds. The iMD uses its gates and partitions to change the configurations of its internal chambers as its requirements change. Parts of the iMD go offline as these parts restructure their architecture while the other parts of the system maintain their functionality. For instance, the therapeutics module will go offline while it optimizes its structure during which time the diagnostic module maintains its physical position.

As one part of one layer restructures by using the gates and conduits, the functionality of other chambers are preserved, thereby allowing the continuity of the system. This seamless restructuring sequence optimizes specific diagnostic and therapeutic applications.

(VI) Surgical Intervention for Installing and Retrieving iMDs

(15) Endoscopic Surgical Procedure to Install, Service and Remove iMDs and Components IMDs are complex integrated bioengineered devices that require installation into specific parts of the human body in order to effectively diagnose, monitor, regulate and interact with biological systems. One way to install the devices is to perform thoracic surgery. However, this approach is expensive, painful and risky.

With the advent of endoscopic surgery, the preferred method of installation of the iMDs is by making a small incision near the installation location, inserting the iMDs and using endoscopic surgical techniques to place, organize and activate the devices and ancillary components. In some cases, inserting the modules separately and assembling them into a complete modular iMD is performed in vivo. In addition, the installation of tubing between iMDs is done with endoscopic tools in order to connect the devices in a network. External tubing is also fitted to the devices and specific tissues using endoscopic techniques.

Once installed, the iMDs require periodic maintenance, including adding and removing a power supply and specific fluids and computation modules. The use of endoscopic surgical procedures is an ideal way to service iMDs without major surgical intervention. In addition, since it is far easier to recover from endoscopic surgery than conventional surgery, some of these procedures are conducted in a doctor's office as an efficient outpatient procedure at substantial cost savings.

In one embodiment of the present system, the iMDs are used in connection with exploratory endoscopic surgical procedures. In this procedure, a drug is targeted to a specific tissue region by the iMD while the feedback to the intervention is viewed by the endoscopic surgery in real time.

(16) Method for Refilling the iMD with "Octopus" Tubing Device

While in the doctor's office, the iMD may be refilled with chemicals by employing an octopus tubing apparatus that connects to the iMD. After first extracting specific chemicals from targeted chambers, the octopus tubing connects to the device at several points on one façade. The chambers are flushed with a neutral fluid and again the fluids are extracted. Finally, the device chambers are filled with a fresh batch of pre-measured chemicals and biologicals. This routine tune-up is periodically required to maintain therapeutic functionality.

Because the modules periodically restructure their geometrical configurations, the device is required to reset to the original position while these fluids are refilled in order to maintain consistency.

(VII) Fabrication Methods of iMD Apparatuses

(17) Layering and Fitting Processes for Assembly of iMDs

IMD architecture resembles a building with sides, layers, specialized compartments and functional networks for plumbing and electrical components. In this sense, the iMD is analogous to a complex fluidic 3D semiconductor. Consequently, the iMD borrows construction techniques from the chip fabrication industry.

The iMD is built in layers from the ground up by using lithographic and self-assembly techniques. While the semiconductor industry is in the process of developing and implementing sub-45 nanometer scale fabrication techniques, the iMD features operate in the sub-micron 100-nanometer to micron space. Bionano components and nano-scale probes are in the 50 nanometer to 500 nanometer range. The overall iMD dimensions, while they vary, are measured in millimeters and centimeters.

The main semiconductor fabrication techniques to construct the layers of the iMD modules are photolithography, deposition, etching and self-assembly. The method used to construct the tubes, joints, fittings, valves, filters are microstereolithography that create 3D micro devices and component parts.

While semiconductors are generally constructed separately and installed in specific chambers of the devices, chip components are also assembled in specific customized modules.

The iMD is modular, with multiple interchangeable modules connected in layers. Each module is itself comprised of multiple layers. Therefore, the fabrication of the iMD modules is characterized by preparing layers, analogous to a multilayer semiconductor. Like a 3D chip, each layer is prepared individually and the layers are combined in a last stage of assembly. This process resembles building blocks. One advantage of the modular approach is that when one layer or module is dysfunctional, it can be removed and replaced while the overall system is preserved.

Multiple photolithographic techniques are used to etch nano-scale and sub-micron-scale components on glass, ceramic, silicon, hafnium, quartz, plastics, polydimethylsiloxane (PDMS) and alloy materials.

Each module is assembled from pre-fabricated parts in a distinct package, with each layer added and then the sides and top.

While the fabrication methods are important, the original architecture of the iMD design is critical as well. In order to create the best design for each iMD type, it is important to use the electronic design automation (EDA) software that creates the structural design of the iMD, including the specific locations of the routing and floor plan for each module and component. 3D EDA software is employed to design and organize the architecture of iMDs.

While the design of the interior structure of the iMDs is essential, the exterior of the iMDs is composed of flexible polymer material in order to mold into an ergonomic shape that integrates with the internal body location. Each iMD is customized to a specific position in the body.

IMDs may be produced in various sizes to correspond to specific application categories.

(18) Self-Assembly Techniques to Fabricate Components of iMD

Some components of iMDs are fabricated by employing novel self-assembly techniques. The process begins with a layer of material that contains pores. An epoxy liquid is poured over the layer and the pores are filled in. The locations of specific pores are marked and gates are installed in the recessed pores at these locations.

In other processes, a conducting metallic chemical (gold or silver) is poured onto an etched network of conduits, with the excess chemical poured off.

(19) Method for Fabricating Microfluidic Conduit System in iMD

While the 3D chip analogy shows the similarity of building the interconnect network for the electrical conduits of the iMD, the analogy breaks down in describing the plumbing network of the iMD.

The creation of microfluidic conduits is performed by etching a network of channels into layers at specific locations. These layers are then precisely sandwiched by mating pins to create conduits. Micro-piping apparatuses are laid with nanotubes at specific junctions. These nano-tubes are constructed by photolithographic techniques and hollowed out to create specific sized pipe segments. These tube segments are used to connect between layers at regular intervals and are located along the sides and in the corners of each module.

In addition to traditional lithographic, etching and deposition fabrication techniques to create channels in layers of substrate fabric to create integrated piping, the system also uses nano assembly techniques to construct sub-micron scale plumbing components. The system specifies the construction of nanodevices such as filters and thin tubes by using nano-assembly techniques of building concentric metallic molecules.

(20) Method for Fabricating System for Electrical Interconnect Fabric in iMD

Much like method of constructing electrical conducting interconnects in semiconductors, the electrical interconnect network of the iMD module layers are constructed by integrating photolithographic techniques to combine specific metals.

Electrical interconnect wires are integrated into each layer to connect computing components, actuators, valves, pumps, filters, sensors and other components.

Semiconductors are installed as the layers are fitted together.

In another embodiment of the system, semiconductors (or their components) are fabricated simultaneously with the creation of specific layers of the system.

Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

DETAILED DESCRIPTION OF THE DRAWINGS

The iMD consists of multiple components. The iMD may be modular or integrated. In one configuration, the main components are the diagnostic module, the therapeutic module and the analytical module. Multiple modules may be combined in specific configurations to construct an iMD. For example, there may be one analytical module, two diagnostic modules and three therapeutic modules. While the modules work together to perform analyses, diagnoses and therapy, respectively, it is possible with multiple modules in a single iMD to perform multiple functions to solve different pathologies simultaneously. This description elucidates the architecture and operations of the iMD components.

Figure 1:
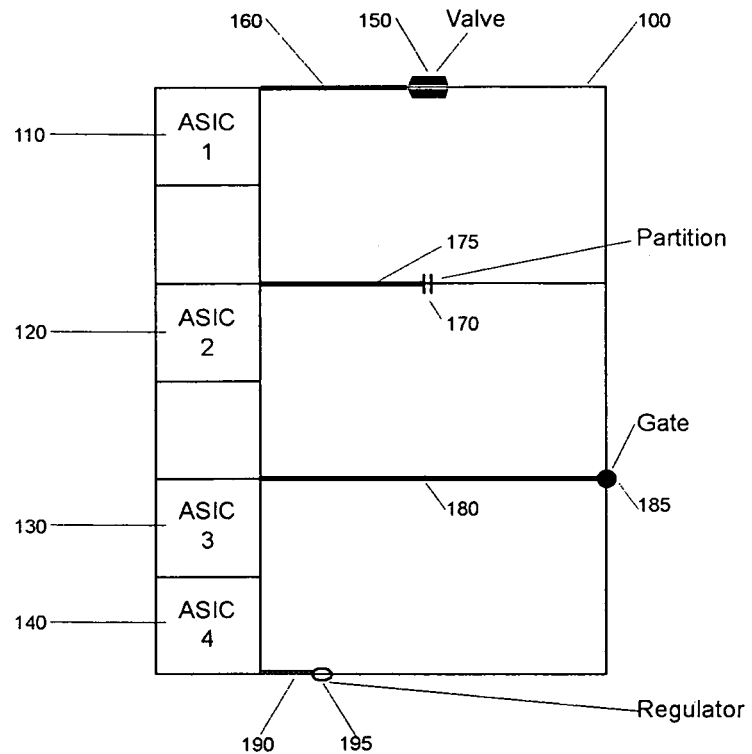
FIG. 1 is a schematic diagram showing one configuration of a diagnostic module of an iMD.

FIG. 1 illustrates a two dimensional view of the diagnostic module (100). In this drawing, there are several partitions that separate the chambers and components in the module. At 110, 120, 130 and 140, application specific integrated circuits are identified, which perform specific tasks. In another embodiment, the integrated circuits are FPGAs, microprocessors or system on chip (SoC) apparatuses, or some combination of these chips. In the drawing, the ASICs control specific functions such as opening and closing a valve (150), opening and closing a partition (170), opening and closing a gate (185) and opening and closing a regulator (195). The connections between the ASICs and the devices are noted at 160, 170, 180 and 190. The diagnostic module is in actuality three dimensional. In one configuration, the diagnostic module has several layers, each with compartments and dividers between chambers are layers. In most cases, a key component of the diagnostic module is the lab on a chip (LOC) which conducts analysis of biological and chemical samples. See FIGS. 11 and 14 below for LOC and µTAS drawings.

Figure 2:
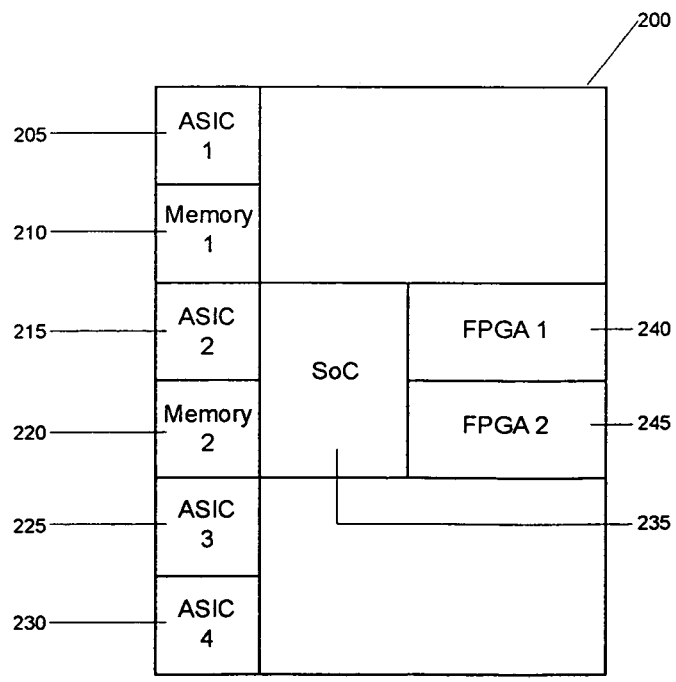
FIG. 2 is a schematic diagram showing one configuration of an analytical module of an iMD.

FIG. 2 illustrates a two dimensional view of the analytical module (200). The main integrated circuit of the analytical module is the SoC (235). However, the analytical module also has two FPGAs (240 and 245) and several ASICs (205, 215, 225 and 230) as well as memory components (210 and 220). The integrated circuits are connected with network interconnections. The two main functions of the analytical module are to collect and store data in a database management system and to perform modeling functions. When the analytical module requires more computer resources, it interacts with external computer resources.

Figure 3:
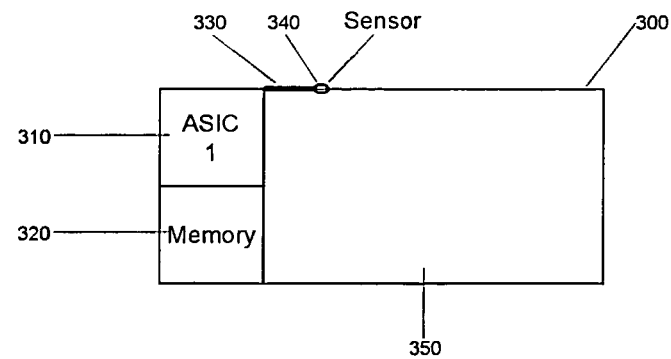
FIG. 3 is a schematic diagram showing an ASIC controlling a sensor and moving data from the sensor to memory.

FIG. 3 shows a sensor component in a module of the iMD (300). The sensor (340) is connected (330) to an ASIC (310) which uses memory (320) to store data about the sensor functions. The sensors are connected in a sensor network to perform specific functions, including self-diagnostic functions in the iMD system. See FIGS. 49-51 for a iMD sensor network description.

Figure 4:
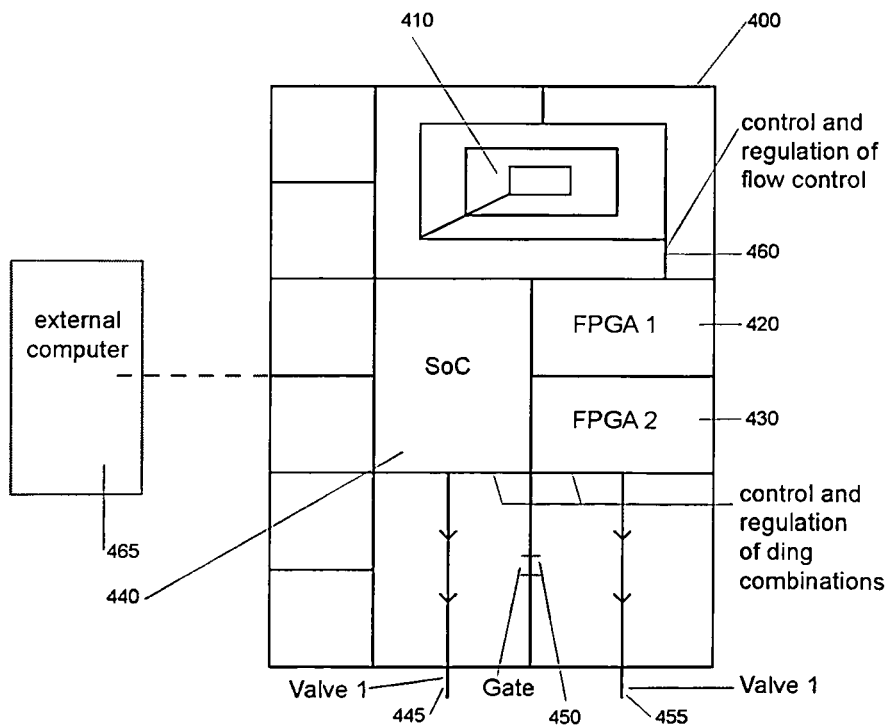
FIG. 4 is a schematic diagram showing one configuration of a therapeutic module of an iMD.

FIG. 4 is a two dimensional drawing of a therapeutic module (400). In the therapeutic module are a SoC (440) and two FPGAs (420 and 430) to control specific regulatory functions. In one compartment (460), the regulation of microfluidic flow control is managed (410) and in other compartments drug combinations are regulated. The compartments are connected by a gate (450) and drugs are dispersed at the valves (445 and 455).

Figure 5:
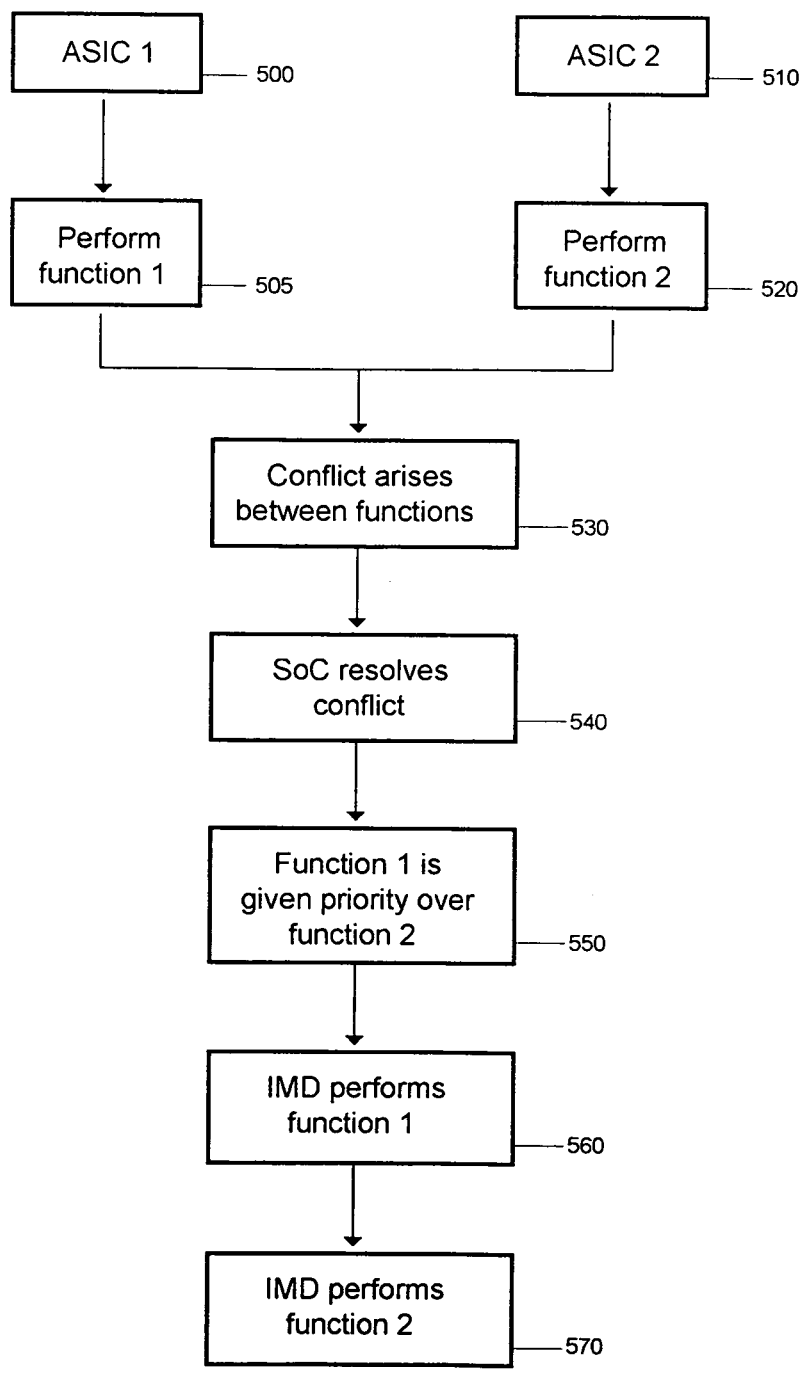
FIG. 5 is a flow chart describing the process of a SoC resolving conflicts in an iMD.
Figure 6:
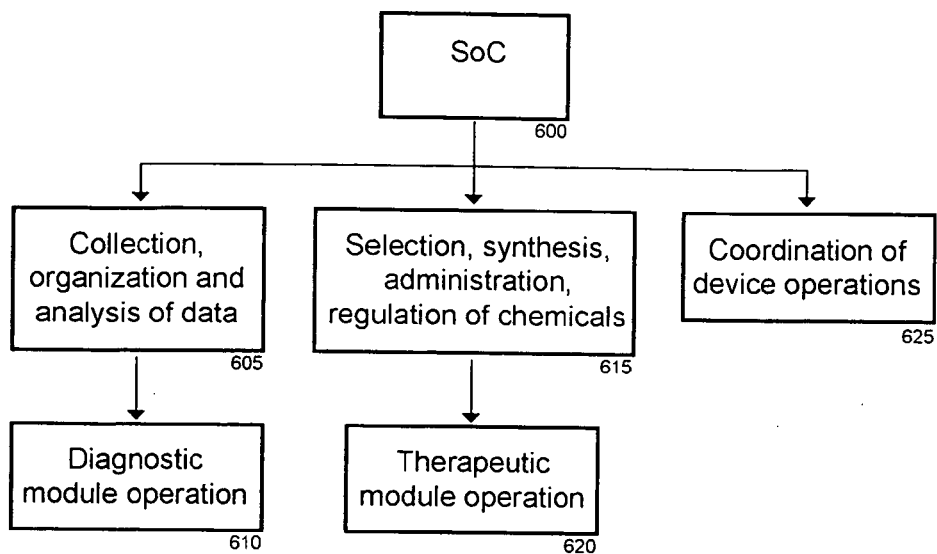
FIG. 6 is a flow chart describing the process of a SoC organizing functions of a diagnostic and a therapeutic module operation.

FIG. 5 shows the process of a SoC resolving conflicts in an iMD. While ASICs 1 (500) and 2 (510) perform functions (505 and 520), a conflict arises between the functions (530) and the SoC resolves the conflict (540). Function 1 is given the priority over function 2 (550) and the iMD performs function 1 first (560) and then performs function 2 (570). FIG. 6 shows the process of the SoC organizing functions of a diagnostic and therapeutic module. The SoC (600) organizes the collection, organization and analysis (605) of diagnostic module operation (610), the selection, synthesis, administration and regulation of chemicals and biologicals (615) at the therapeutic module (620) and coordination of device operations (625).

Figure 7:
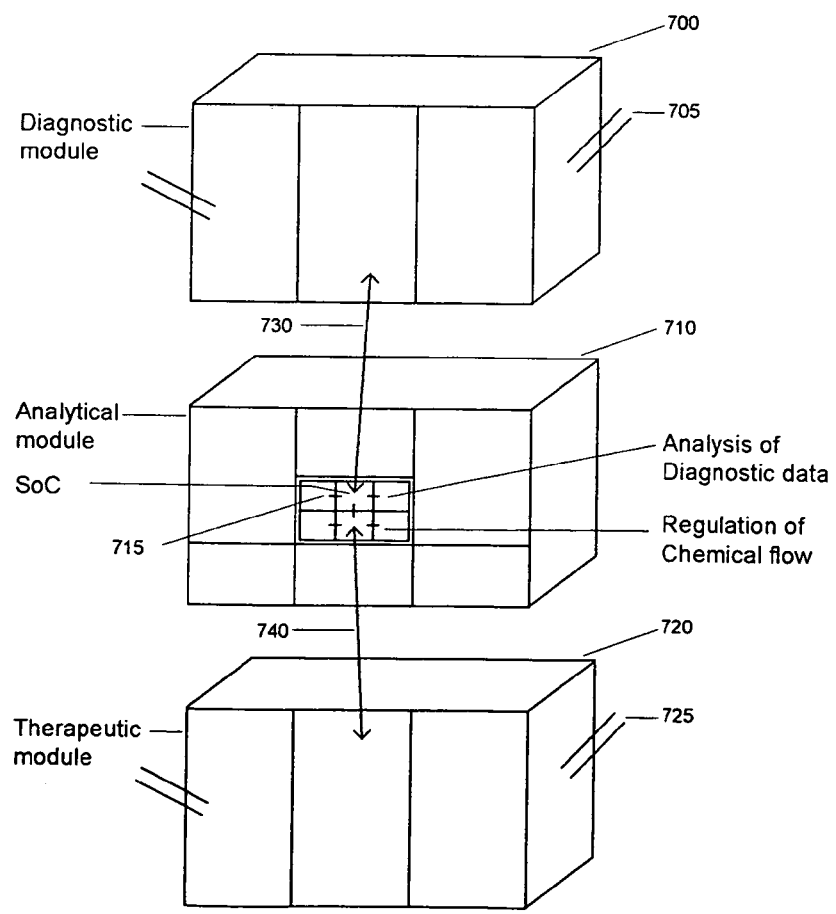
FIG. 7 is a schematic diagram showing a cut out of the diagnostic module, the analytical module and the therapeutic module.

FIG. 7 is a cut out of the diagnostic, analytical and therapeutic modules. The SoC (715) at the center of the analytical module is connected (730 and 740) to the other modules and performs both the analysis of the diagnostic data from the diagnostic module (700) and the regulation of chemical flow in the diagnostic and therapeutic modules (720).

Figure 8:
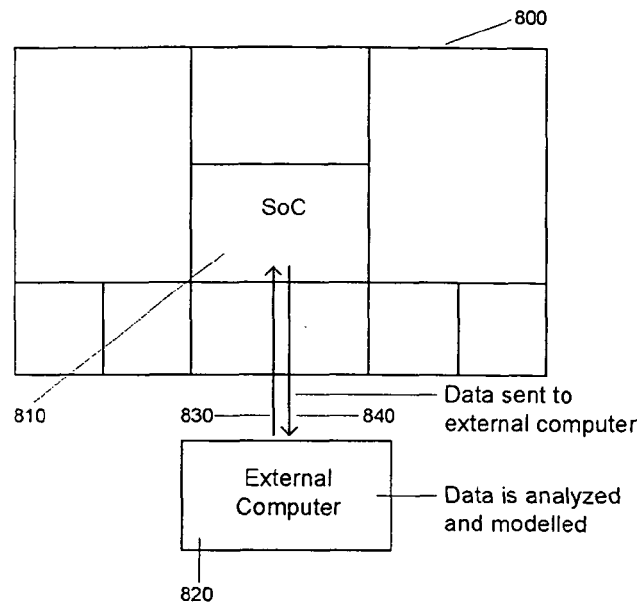
FIG. 8 is a schematic diagram showing the analytical module of an iMD interacting with an external computer.

FIG. 8 shows the interaction of the analytical module (800) with an external computer (820). The SoC (810) is shown in the center of the analytical module. As data is sent to the external computer (840), it is analyzed and modeled and then returned (830) to the analytical module.

Figure 9:
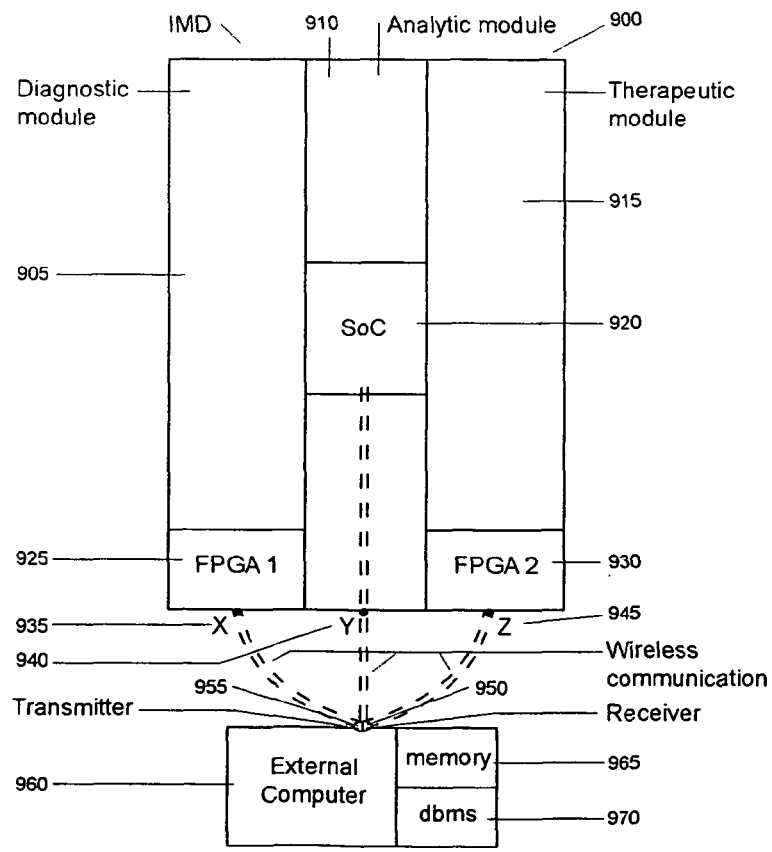
FIG. 9 is a schematic diagram showing the interaction of multiple integrated circuits in an iMD interacting with an external computer.

FIG. 9 illustrates the combination of the diagnostic (905), analytical (910) and therapeutic (915) modules in an iMD (900). An SoC (920) is in the center of the analytical module. FPGA 1 (925) and FPGA 2 (930) are shown in the diagnostic and therapeutic modules, respectively. The integrated circuits are wirelessly communicating with external computer resources (960), with a receiver (950) and transmitter (955). The wireless transmitters and receivers of the iMD modules are shown at X (935), Y (940) and Z (945).

Figure 10:
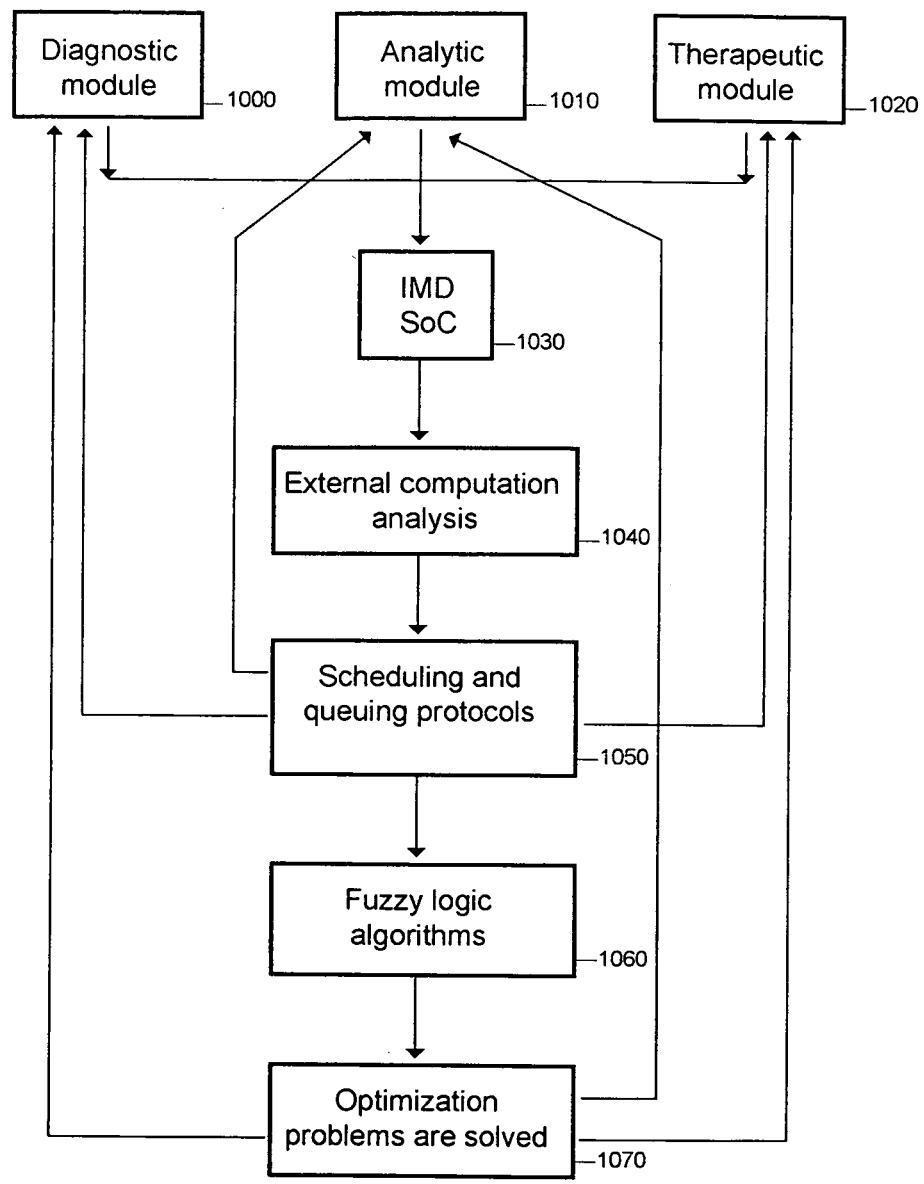
FIG. 10 is a flow chart showing the process of operations of the iMD.

FIG. 10 shows the process of iMD operations. The diagnostic (1000), analytical (1010) and therapeutic (1020) modules process data in the SoC (1030) and in external computation resources (1040). The computer resources produce scheduling and queuing protocols (1050), which are fed back to the individual iMD modules, to process instructions from the iMD components and apply fuzzy logic algorithms (1060) until the optimization problems are solved (1070) in a time sensitive way.

Figure 11:
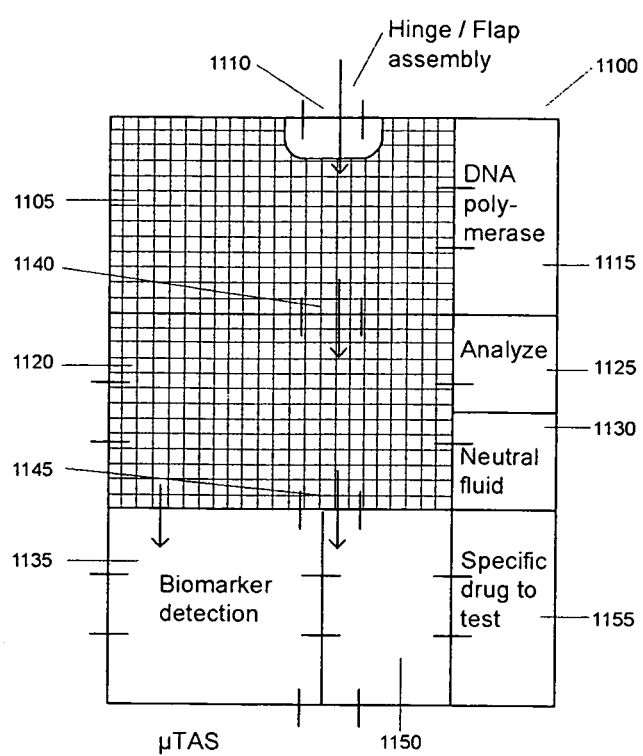
FIG. 11 is a schematic diagram showing the μTAS component of the diagnostic module of a iMD.

FIG. 11 shows a top view of the micro total analysis system (µTAS) component of the diagnostic module (1100). The diagnostic module consists of a set of chambers, one compartment in which the µTAS is situated. At 1105 and 1120 are a set of screens to test biologicals such as DNA, RNA or cell samples. DNA polymerase is stored in a chamber next to the screens (1115) as is analyte (1125), a neutral fluid (1130) and a specific drug to test (1155) the sample. Biomarkers are detected at a specific chamber (1135). The chemicals and biologicals are transported through the device in a series of microfluidic channels, gates and valves.

Figure 12:
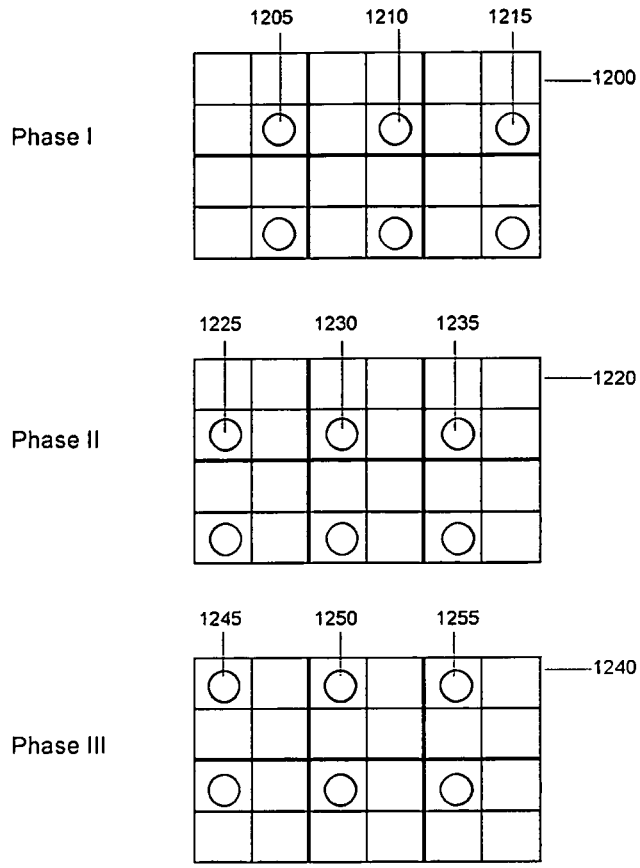
FIG. 12 is a set of schematic drawings showing the use of different analytes in wells of a grid of chambers with a movable screen that confines the analyte to a specific well for a specific operation at each phase.

FIG. 12 shows three phases of operation of a set of wells in a grid of chambers with a movable screen that confines the analyte to a specific well. In this example, the grids are configured into four separate wells of six sets each. In phase I, the screen covers the three wells of the set of four wells per set thereby allowing an analyte into only the selected wells (1205, 1210 and 1215 shown at the top layer) at the bottom right. In phase II, the screen covers the three other wells and allows the bottom left wells to be open to receive an analyte (at 1225, 1230 and 1235 shown at the top layer). In the third phase, the top left set of wells (at 1245, 1250 and 1255 shown at the top layer) is open to receive an analyte. This approach allows a set of wells to be filled with samples and different analytes applied to sets of wells to accelerate the testing of multiple samples simultaneously.

Figure 13:
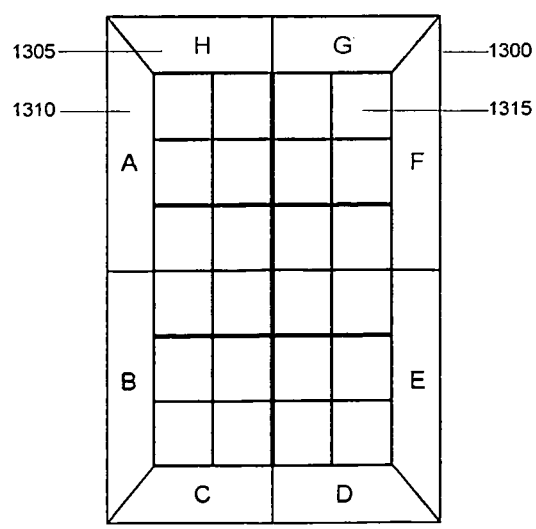
FIG. 13 is a schematic diagram showing a μTAS module layer with periphery storage for eight different chemicals and biologicals.

FIG. 13 shows the μTAS layer (1300) of a diagnostic module in which the center chambers (1315) are open compartments to allow the combination of different biologicals and chemicals for testing, while the periphery compartments A-H (1305) are used to store specific biological or chemical substances. The specific substances are guided into specific chambers by the conduits of the microfluidic interconnect system.

Figure 14:
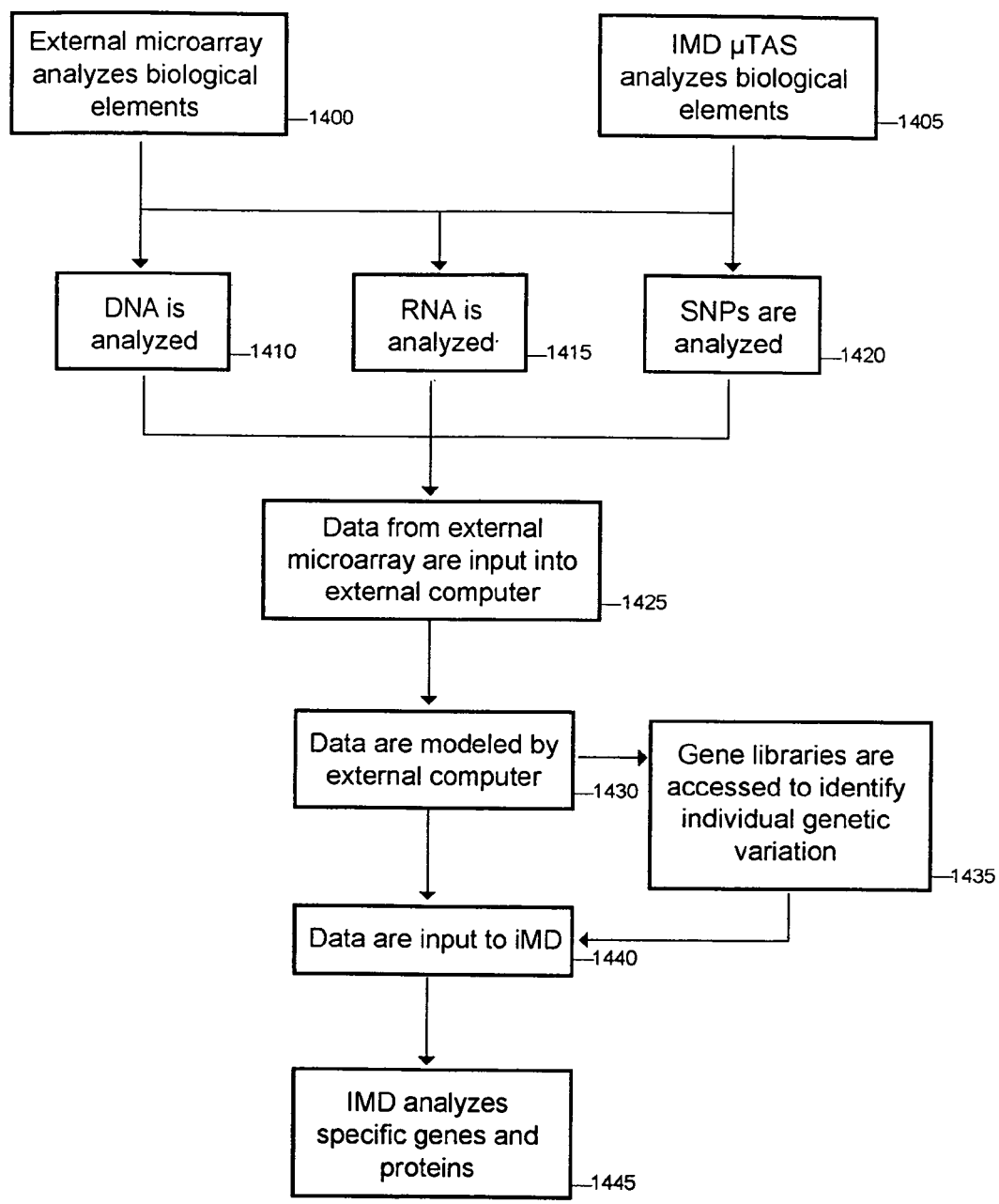
FIG. 14 is a flow chart describing the process of analyzing DNA, RNA and SNPs in internal and external microarrays.

FIG. 14 shows the process of sharing internal iMD μTAS and external microarray analysis components. While the external microarray analyzes biological elements (1400) and the internal iMD μTAS analyzes biological elements (1405), the DNA (1410), RNA (1415) and SNPs (1420) are analyzed and data from the external microarray are input into an external computer (1425). The data are modeled by an external computer (1430) and gene libraries are accessed to identify individual genetic variation (1435). The data are input into the iMD (1440) and the iMD analyzes specific genes and proteins (1445).

The diagnostic module may have different configurations. In one configuration, the diagnostic module has a μTAS layer adjacent to an LOC layer, which is itself adjacent to a layer consisting of compartments that store biological and chemical components used for analysis by the other two layers. This configuration of the diagnostic module allows specific patient biologicals to be tested by the μTAS layer for specific known pathologies with specific analytes, while the LOC is used to experiment with identifying solutions by using a set of optimization metaheuristics.

Figure 15:
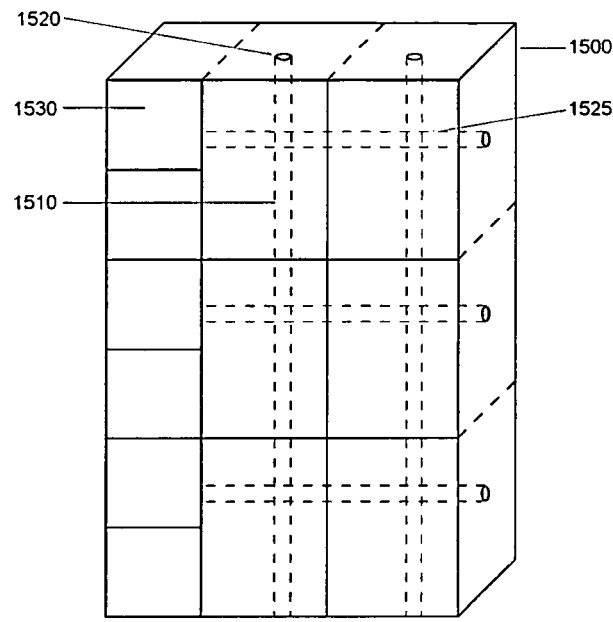
FIG. 15 is a schematic drawing showing the internal tubing of a microfluidic conduit system of a diagnostic or therapeutic module.

Both the diagnostic module and the therapeutic module use chemicals and biologicals on-board to test and solve medical problems. Consequently, there is a need to precisely move specific chemicals and biologicals from compartment to compartment within the iMD. FIG. 15 shows the microfluidic conduits, consisting of internal tubing (1510 and 1525), that are integrated into the diagnostic and therapeutic modules. The microfluidic tubing is placed along the walls of the compartments. At the junction of the tubing and the wall are gates and valves (1520) that allow the chemicals and biologicals to be moved from location to location between compartments. See also FIG. 16 for a view of microfluidic tubing in the therapeutic modules. The microfluidic architecture is a key mechanism for the transmission of chemicals within the iMD. The microfluidic channels, in addition to gates and valves between compartments, also use micro-pumps to move liquids between chambers and components. See FIGS. 18-20 for a description of the micro-pumps.

Figure 16:
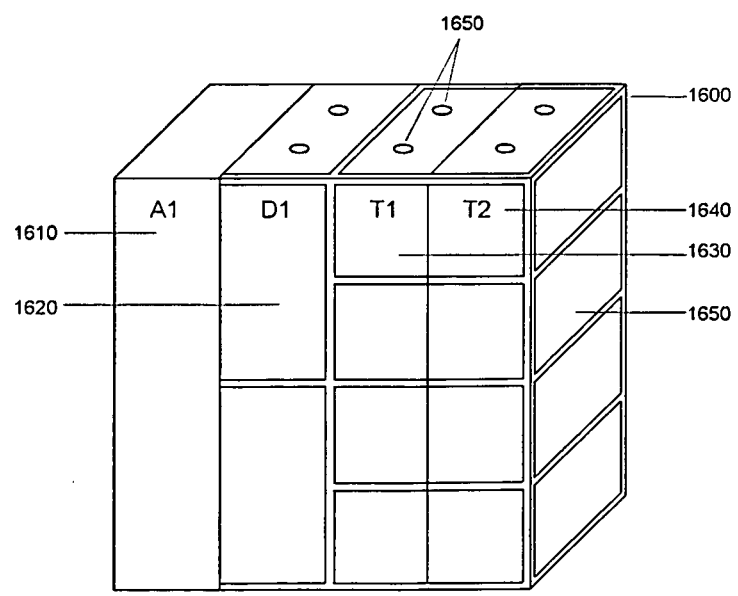
FIG. 16 is a 3D schematic drawing of microfluidic architecture of therapeutic modules in an iMD.

FIG. 16 shows the three dimensional aspect of the iMD (1600) with an emphasis on the microfluidic architecture highlighted in the therapeutic modules (1630 and 1640). The valves to the exterior of the therapeutic modules and diagnostic module (1620) are shown (1650 for T1), while the tubing is shown as double lines (1650).

Figure 17:
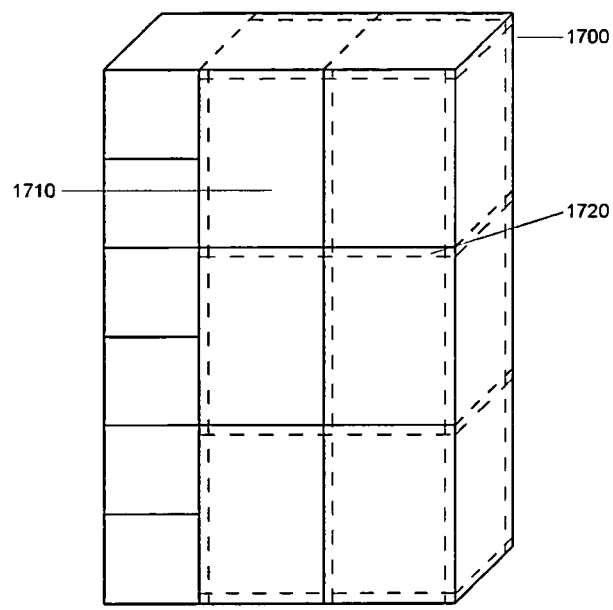
FIG. 17 is a schematic drawing of the interconnect network of an iMD.

Not only does the iMD main components require microfluidic conduits, but the electrical connections between components are maintained by an interconnect network. FIG. 17 shows the interconnects (1720) in three dimensional representation of a single module (1700) that connects the various chambers (1710). The interconnects are along the edges of the chamber walls. The analogy of the interconnects in the iMD are to semiconductor interconnects. The internal electrical network connects the components and the semiconductors to allow functionality.

Figure 18:
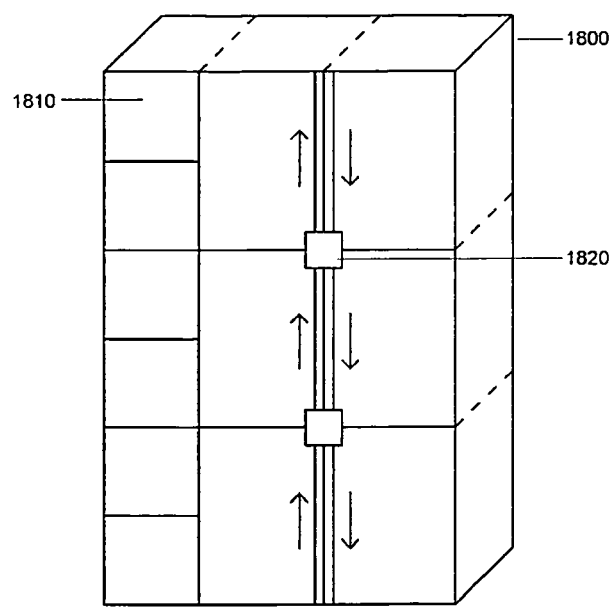
FIG. 18 is a schematic diagram showing the micro pump assembly configuration of an iMD module.
Figure 19:
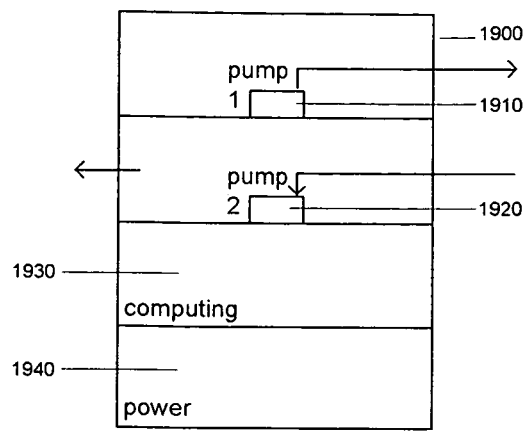
FIG. 19 is a schematic diagram showing a configuration of a two pump model.
Figure 20:
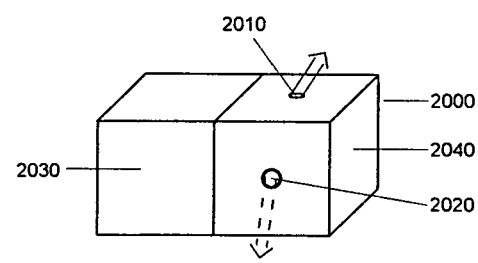
FIG. 20 is a schematic drawing of a micro pump.

FIG. 18 shows the micro-pump assembly. The micro-fluidic conduits (1810) of a module are intersected by a set of micro-pumps (1820) spaced at the junction of each set of compartments. As FIG. 19 shows, the two pumps (1910 and 1920) either push or pull fluids. In another embodiment, the two pumps work together to push and pull fluids in order to promote flow control. In this illustration of the side view of a diagnostic module, the computing (1930) and power (1940) components are shielded in separate compartments to maximize functionality. FIG. 20 shows the external compartment of a micro-pump (2000), which sends fluid in one cavity (2010) in one use of the pump and sends fluid in another direction in another cavity (2020). The pump mechanism uses suction to perform the pumping function and is enclosed at 2030.

In another embodiment of the present system, the iMD uses components that enable fluidic transfer with an air-bursting detonator.

In some embodiments of the iMD, there are at least two separate batteries to operate different functions or to act as power reserve. In one example, one battery operates the main iMD functions, while other batteries provide specific functional performance such as providing a shock to a patient. An iMD may administer an electric shock in a muscle or to the heart or brain to perform a function.

Figure 21:
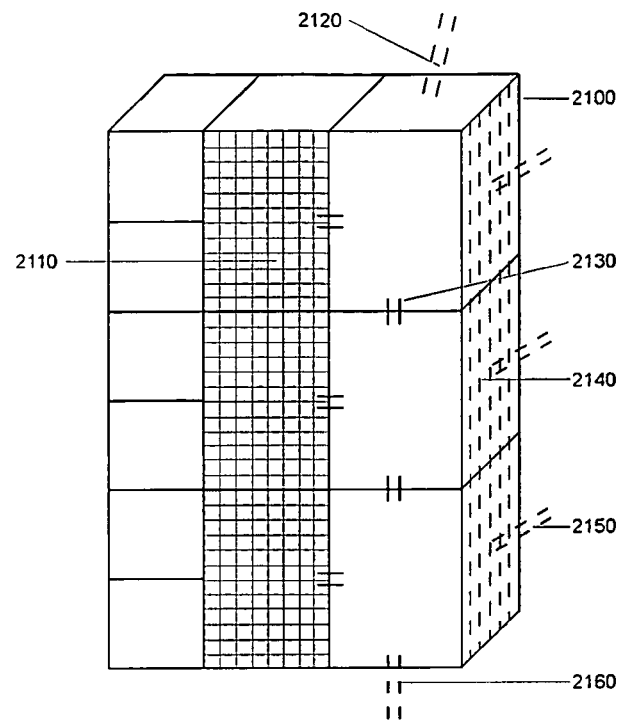
FIG. 21 is a schematic drawing of a diagnostic module with five layers.
Figure 22:
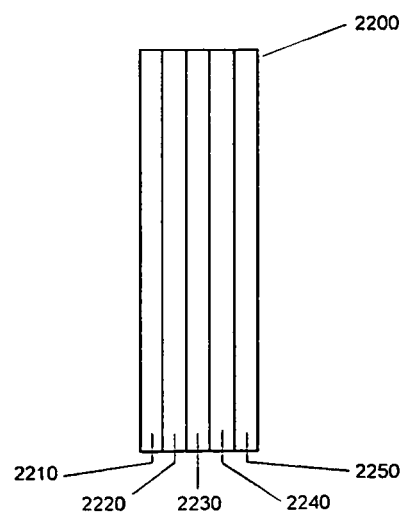
FIG. 22 is a schematic figure of the side view of a five layer diagnostic module.

The diagnostic module is shown in a three dimensional illustration at FIG. 21. In this example, the module has five layers to accommodate the μTAS, the LOC and the holding compartments. In one embodiment, there are more than one LOC on two or more layers. The grid mechanism illustrated (2110) is for analysis of chemicals and biologicals, while the compartments at the right side are used to store and transmit chemicals and biologicals between the compartments of the layers of the module. The left side is used by the semiconductors for control of the microfluidic and analytical functions. The internal valves (2130) are used to transport chemicals and biologicals between the compartments of the module, while the external valves (2100, 2150 and 2160) are used to transport chemicals and biologicals between the module and other modules as well as external tissues. FIG. 22 is a side view of the five layer diagnostic module.

Figure 23:
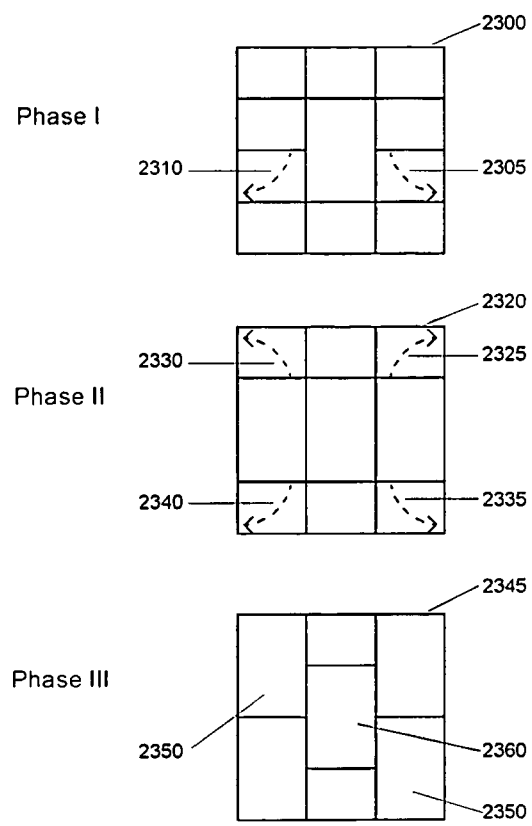
FIG. 23 is a schematic diagram showing the several phases of the restructuring of partitions of a therapeutic module.

In order to accomplish a range of multifunctional tasks, the therapeutic module is capable of reconfiguration. In this sense, the therapeutic module is organized like a complex programmable logic device (CPLD), yet the therapeutic module contains, in addition to an electrical interconnect network, a microfluidic network of channels that also require architectural transformation. FIG. 23 shows the process of the restructuring of the partitions of the therapeutic module. At phase I, the module (2300) uses partitions that swing like a gate from position to position (at 2305 and 2310). At phase II, the module's partitions again move to new positions (2325, 2330, 2335 and 2340) until, at phase III, the module stops restructuring once it achieves its goal of a specific architectural configuration.

Figure 24:
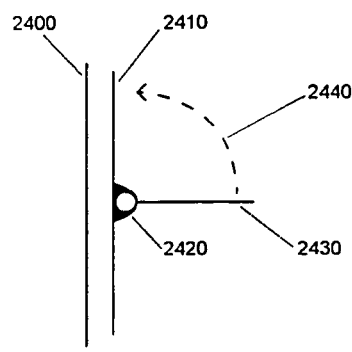
FIG. 24 is a drawing of a movable ball joint.

FIG. 24 shows a movable ball joint (2420) component that is used to swing the partitions from position to position to accommodate the transformation process. The ball joint is positioned on a double layered wall between 2400 and 2410 in order to allow fluids to move in the channel of the microfluidic conduit.

Figure 25:
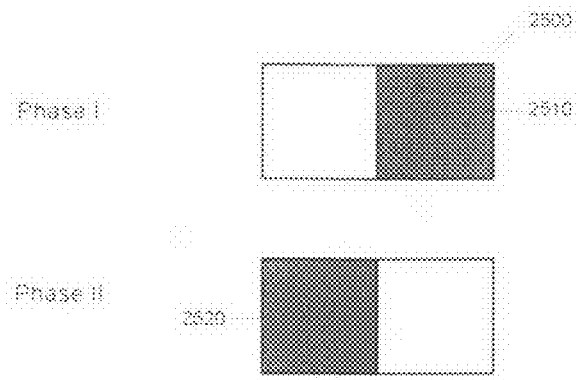
FIG. 25 is a drawing of two phases of a screen moving from position to position.
Figure 26:
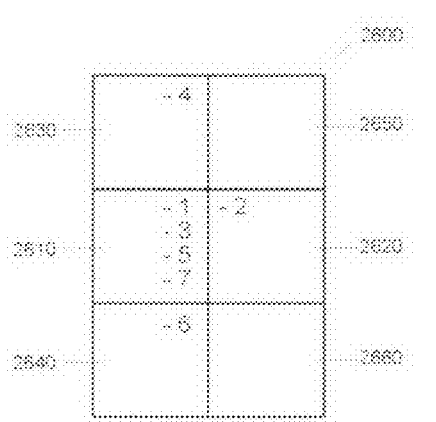
FIG. 26 is a schematic diagram showing the order of movement of screens to perform a set of functions.
Figure 27:
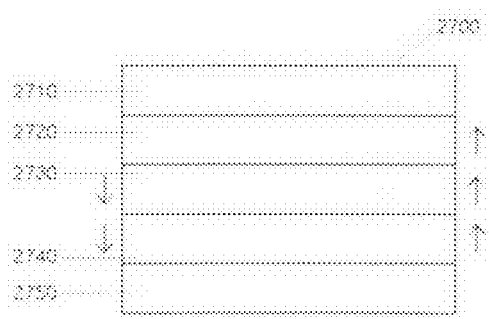
FIG. 27 is a schematic diagram showing the side view of one chamber of a diagnostic module in which screens move up and down to modify the module configuration.

In addition to partitions that move with ball joints, iMD modules employ a screen moving from position to position. In FIG. 25, the screen moves from 2510 in phase I to 2520 in phase I. The screen is used in the diagnostic module to allow wells to be blocked. In FIG. 26 the movement of the screens in a six panel compartment of a module is shown. The screen moves initially from panel 2610 to 2620 and then back to 2610. In a next movement, the screen moves from panel 2610 to 2610 and then back to 2610. In the next movement, the screen moves to panel 2640 and then back one last time to 2610. The screen moves on a plane of the panels sliding between pre-set grooves. In FIG. 27, the screen is shown to move up and down between layers. In this side view of the layers (2700) of a module, the screen moves in a similar way to a CD changer that reshuffles its CDs from one layer to another.

Figure 28:
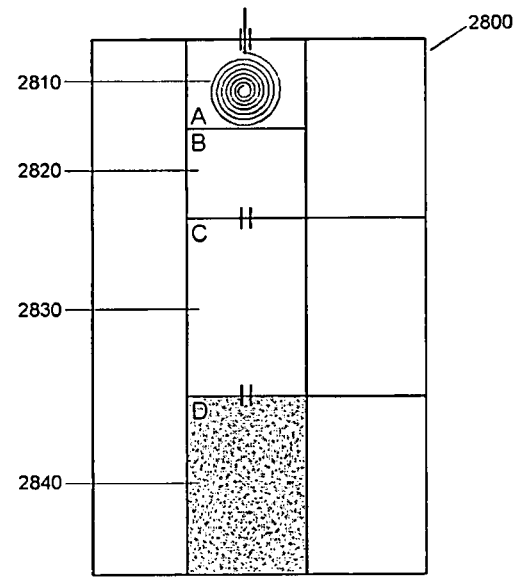
FIG. 28 is a schematic diagram showing the storage of retractable probes, biologicals, analytes and nano- or microdevices.

The diagnostic module is able to store multiple components. In FIG. 28, the compartments in the middle row of the diagnostic module (2800) is shown with retractable probes (2810), biologicals (2820), chemicals (such as analytes) (2830) and nanodevices (2840). Nanodevices include nanorobots (for probes and cargo carrying devices) as well as nanoparticles.

Figure 29:
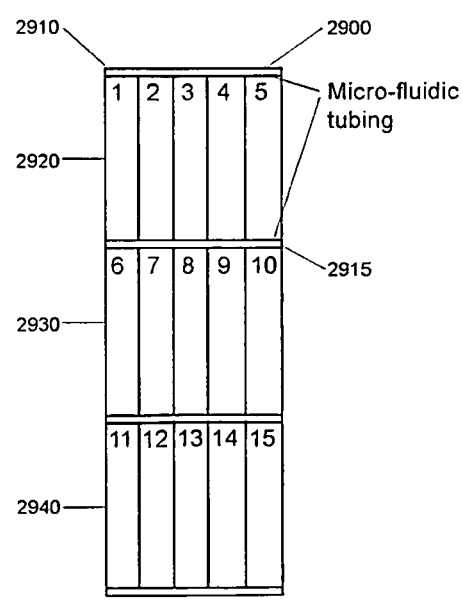
FIG. 29 is a schematic diagram showing a side view of a therapeutic module with a configuration of fifteen storage compartments.
Figure 30:
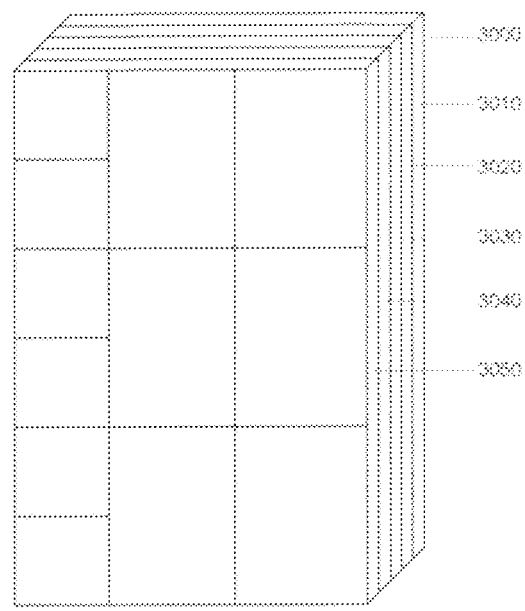
FIG. 30 is a schematic diagram showing five layers of a therapeutic module.
Figure 31:
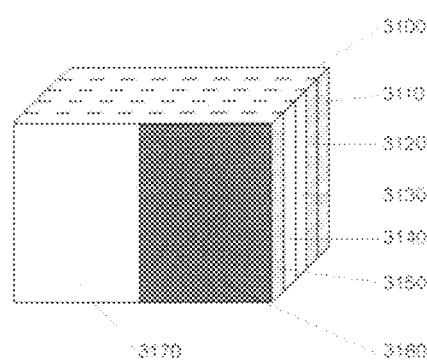
FIG. 31 is a schematic drawing showing a side view cut out of one chamber of a module.

FIG. 29 is a side view of a five layer therapeutic module (2900) showing the storage of fifteen different components in each set of compartments. The chemicals, biologicals and nanodevices are moved from compartment to compartment by using the micro-fluidic tubing (2910 and 2915). FIG. 30 shows a five layer therapeutic module (3000). This drawing is a view of the "gates" that move, similar to screens, from compartment to compartment to facilitate a transformation of the structure of the components. In this case, the gates move like a declining or ascending garage door folding down from an adjacent plane. One gate moves from 3160 to 3150 and another gate moves from 3110 to 3120.

Figure 32:
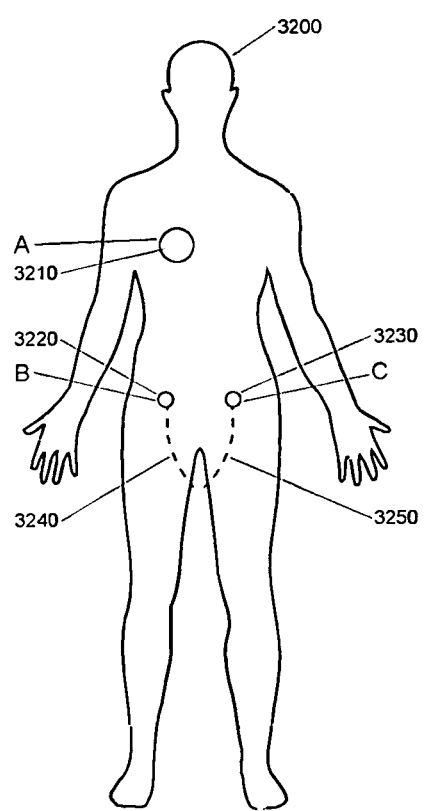
FIG. 32 is a drawing of a patient with an iMD and two satellite medical devices.

FIG. 32 shows an iMD (A) installed in a patient's chest (3210) and two satellite devices (B and C) installed in the abdomen (3220 and 3220) with connections to external locations (3240 and 3250).

In order to facilitate the structural transformation of the therapeutic module to accommodate multi-functional applications, the iMD borrows a software design technology of electronic design automation (EDA) from the semiconductor industry. While the layout of routing architectures of electronic interconnect networks by EDA software is useful for semiconductors, the use of EDA for the iMD is complicated by the microfluidic components. Nevertheless, because the iMD has several layers of components, 3D EDA software is applied to the process of organizing and reorganizing components of the iMD modules for multiple uses on demand. This process of transformation by using EDA facilitates automated prototyping of specific medical solutions to unique problems and constitutes a novel application of evolvable hardware.

Figure 33:
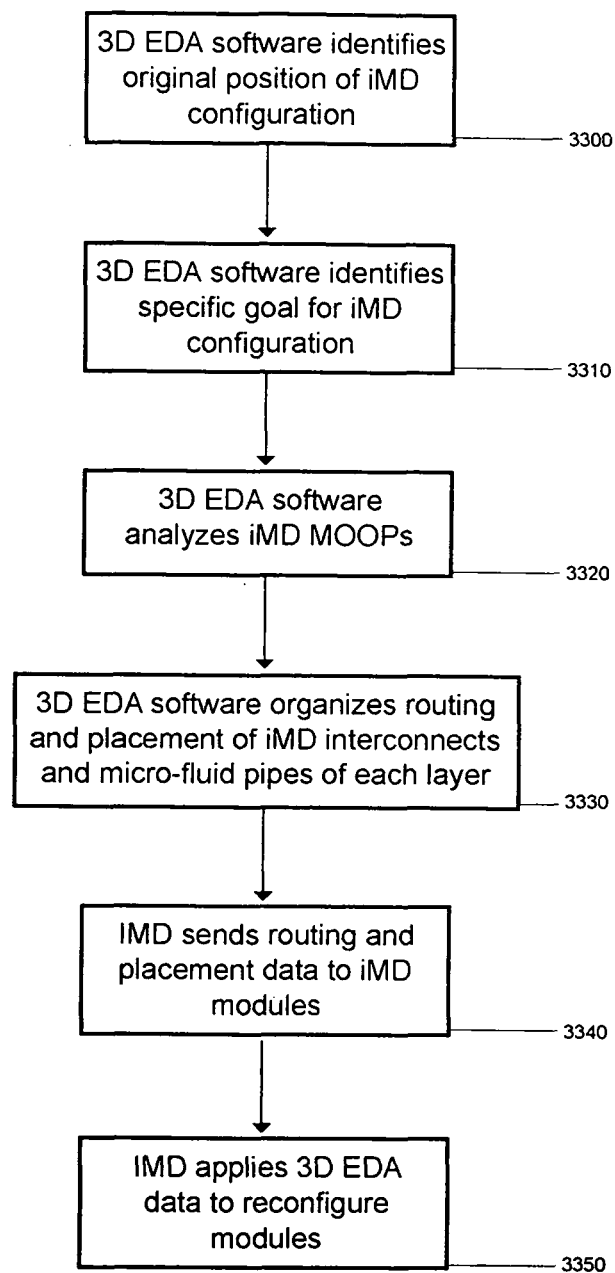
FIG. 33 is a flow chart describing the process of using EDA software to configure modules in an iMD.

In FIG. 33, the process of using EDA software to restructure the therapeutic module configuration is described. After the 3D EDA software identifies an original position of the iMD configuration (3300), the software identifies a specific goal for the iMD configuration (3310) and analyzes the iMD MOOPs (3320). The 3D EDA software then organizes the routing and placement of iMD interconnects and micro-fluid pipes of each layer (3330) and the iMD sends the routing and placement data to iMD modules (3340) for application of the 3D EDA data to reconfigure its modules (3340).

Figure 34:
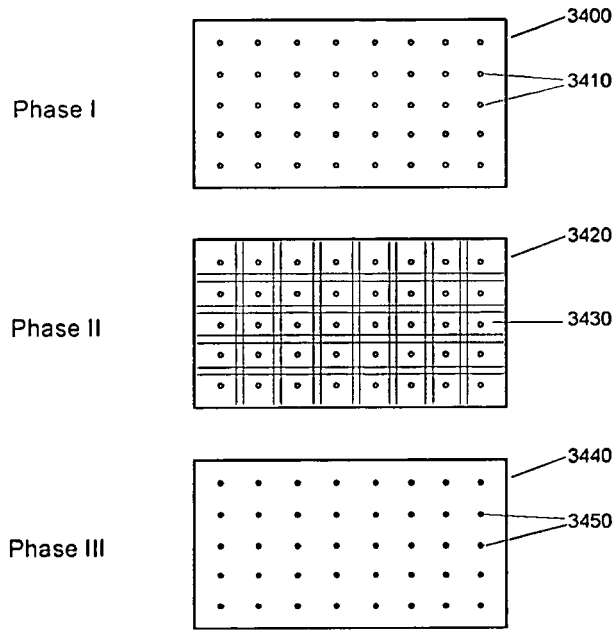
FIG. 34 is a set of drawings to depict the three phases of epoxy used to fill in holes in construction of a module in an iMD.

The fabrication of the iMD modules is performed in layers. Each layer is constructed and then combined with other layers. In FIG. 34, the three stages of constructing a single layer of the diagnostic module is described. In the first phase, a layer (3400) has forty holes punched on a grid. At phase II, the layer has epoxy placed over the layer (3430), which is then poured off. In phase three, the epoxy fills the holes (3450) to create wells in the holes that allow liquids to be poured on and off the layer.

Micro-fabrication methods used in the iMD system include plasma etching, reactive ion etching, ion beam milling, chemical-vapor deposition, micromachining, 3D surface micromachining, dry-bulk surface micromachining and multi-layer soft lithography techniques.

Figure 35:
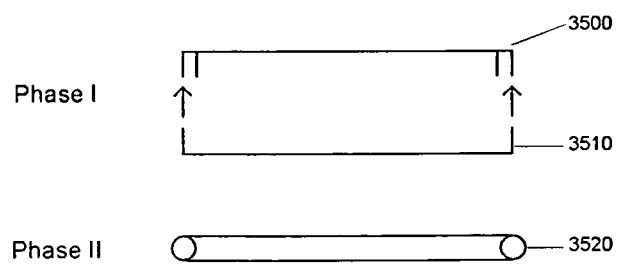
FIG. 35 is a schematic diagram showing the two phases of construction of a micro pipe assembly.

Pipes are created in the microfluidic conduits by combining pipe sections (3500 and 3510) as illustrated in FIG. 35. The finished pipe mechanism is shown at 3520. The pipe components carry fluids in the pico-liter range.

Figure 36:
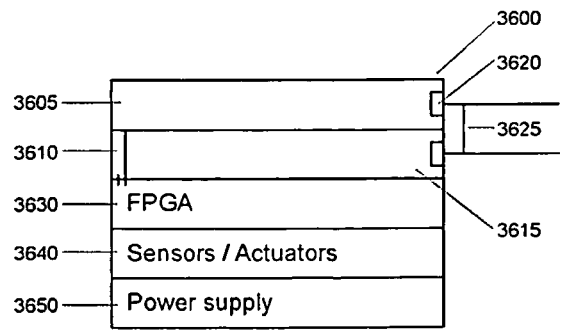
FIG. 36 is a schematic drawing showing the side view of the layers of a module in an iMD.

A side view of a five layer module (3600) in an iMD is shown in FIG. 36. The power supply (3650) is shown on one layer, the sensors and actuators are shown on another layer (3640), an FPGA (3630) and the compartments are shown on the top two layers (3605 and 3615). The microfluidic conduits are shown connecting the top three layers (3610) and the external valves (3620) are shown in the top two layers (3620) to import and export fluids to and from tissues. The layers of the modules may each contain semiconductors, sensors and power supply in one configuration. However, in another configuration, each layer comprises a different functional component. This flexibility allows the iMD to solve multiple pathologies simultaneously.

Figure 37:
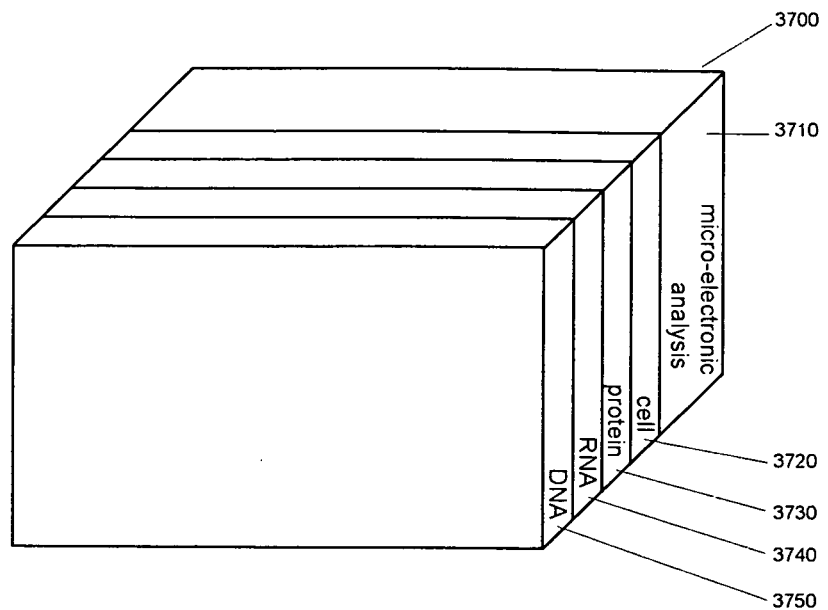
FIG. 37 is a schematic diagram showing the multiple layers of a microarray device component of an iMD.

FIG. 37 shows one configuration of the multiple layers of a µTAS device embedded in the diagnostic module of an iMD. In this configuration, different layers comprise storage for DNA (3750), RNA (3740), protein(s) (3730) and cells (3720). The biologicals are moved through the micro-fluidic conduit system to the µTAS layer for analysis and testing of specific substances with analytes.

Figure 38:
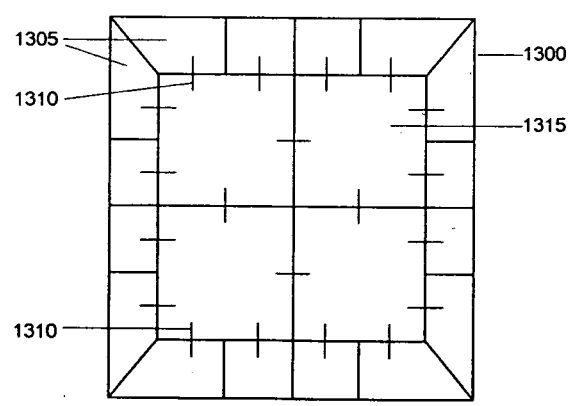
FIG. 38 is a schematic drawing showing compartments of an iMD in which two or more chemicals or biologicals are mixed on-demand.

FIG. 38 shows a top view of a layer (3800) of a module in which the chemicals and biologicals are stored on the perimeter of the layer (3810). As specific chemicals and biologicals are required, the system opens a perimeter gate and moves the chemical or biological to an inner chamber (3820, 3830 or 3840) for mixture on demand. Pumps are used to apply pressure to mix the liquids. Once the phase of the process is over and the test completed, the chemicals are flushed from the system using the microfluidic conduit system and the chambers are flushed with a neutral liquid for cleaning.

Figure 39:
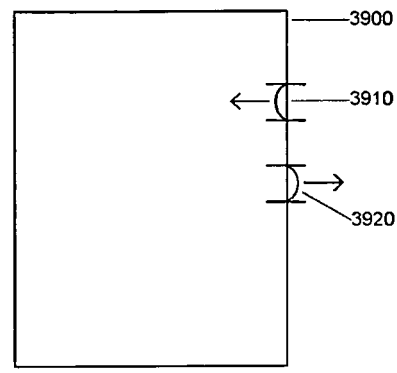
FIG. 39 is a diagram showing the operation of unidirectional valves in an iMD module.

In order to move liquid from one chamber to another, valves are used. FIG. 39 shows the use of valves to import (3910) and export (3920) chemicals into and out of a compartment (3900). In this example, the valves are unidirectional. However, the valves may also be bidirectional in another embodiment.

Figure 40:
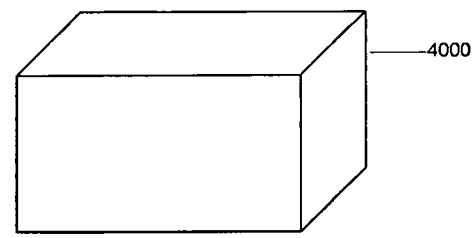
FIG. 40 is a set of diagrams depicting different options of shapes of an iMD.
Figure 40:
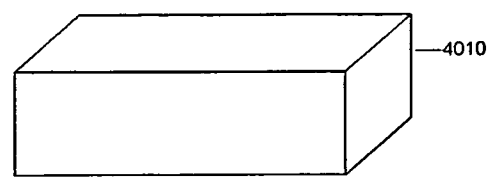
Figure 40:
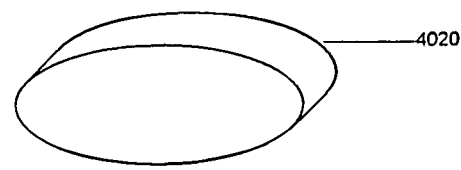

An iMD is customized to each patient. The shape and size of the iMD, as well as satellite devices, is tailored to the specific medical purpose and individual. The iMD comes in extra large, large, medium, small and extra small sizes to accommodate a range of medical situations. Further, the iMD is contoured to accommodate specific body cavity positions. FIG. 40 shows several examples (4000 and 4010) of box shaped iMDs and a rounded oval example (4020).

Figure 41:
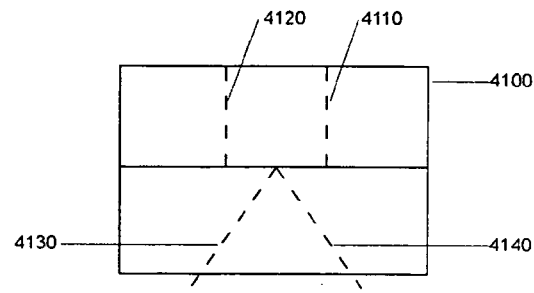
FIG. 41 is a drawing of cubic partitions and gates of a module of an iMD.

The movable gates are shown in FIG. 41 at 4110, 4120, 4130 and 4140. By moving from one position to another, the compartments of each module are reconfigured to accommodate different functions.

Figure 42:
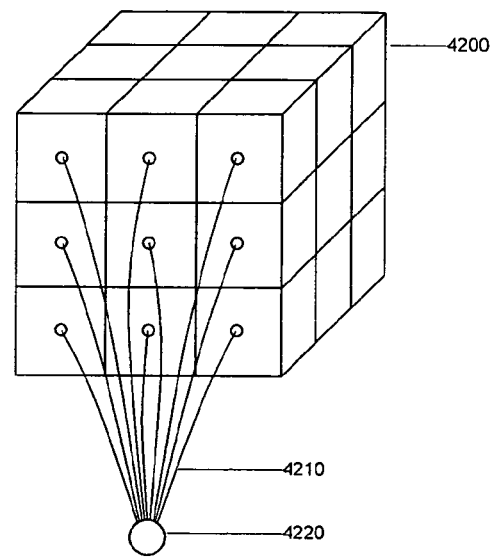
FIG. 42 is a schematic diagram showing octopus connections for an iMD.

FIG. 42 shows the external octopus connections to an iMD. In this three module example, several components from each layer connect directly to the octopus apparatus (4210) which consolidates the lines at 4220. This mechanism provides an efficient way to drain or fill fluids into the iMD.

Figure 43:
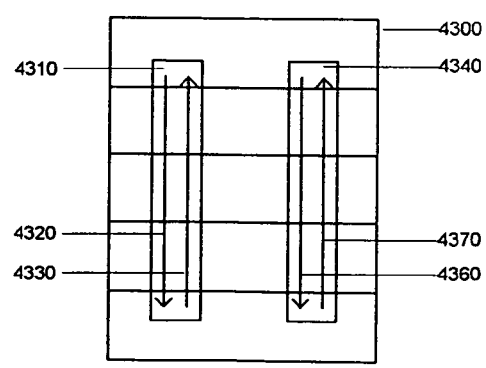
FIG. 43 is a schematic diagram showing elevator shafts on the edges of an iMD that act as routers or conduits for fluids.

FIG. 43 shows internal elevator-type shafts on the edges of a module (4300) of an iMD. The elevator-type shafts facilitate the movement of fluids between layers and acts as routers of fluids.

Figure 44:
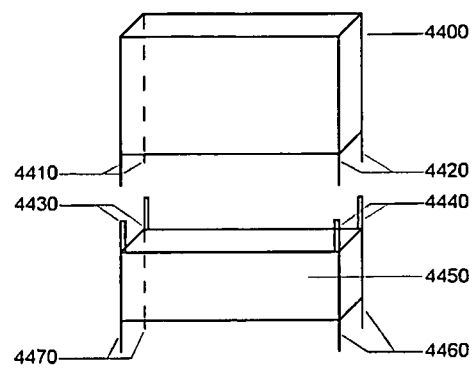
FIG. 44 is a schematic diagram showing the assembly of internal parts of two modules that are connected by pins.

FIG. 44 shows the assembly of specific components with external packaging and pins. The top component (4400) has pins (4410 and 4420) that fit into the female slots (4430 and 4440) of the bottom component (4450). The bottom component (4450) also has pins (4460 and 4470) in order to accommodate a combination with another component.

Figure 45:
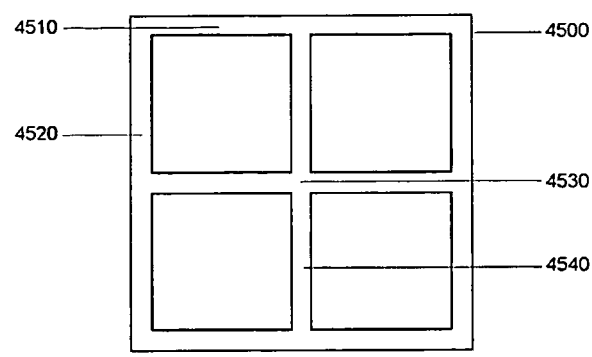
FIG. 45 is a drawing of a floor plan of a layer of an iMD module.

FIG. 45 shows a floor plan of a layer of a module. In this example, the periphery channels, both horizontal and vertical (4510 and 4520), connect to a junction bridge (4540) and to a center channel (4530).

Figure 46:
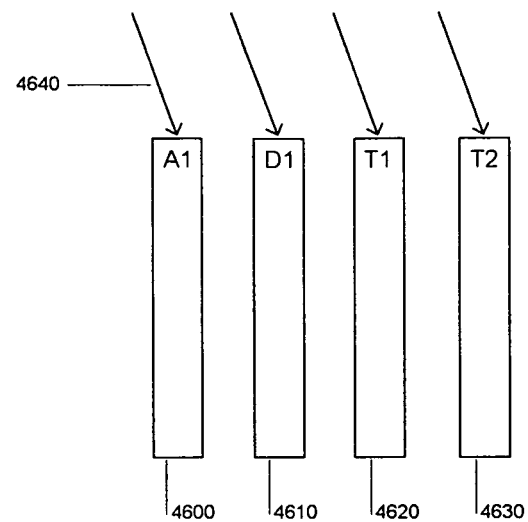
FIG. 46 is a schematic diagram showing modules that are endoscopically installed and assembled in a patient.

In some cases, it is optimal not to install the iMDs by a surgeon by creating a large incision. In these cases, it is best to install the component modules of the iMD endoscopically and then combining the modules in vivo. In FIG. 46, the analytical module (4600), the diagnostic module (4610) and two therapeutic modules (4620 and 4630) are installed separately (4640) and then assembled together once inside the patient. The advantage of this module in not only a quick recovery process for the patient, but when the patient requires a replacement of only a single module or the supplemental addition of additional modules, the iMD may be selectively modified in the patient without removing the whole device.

Figure 47:
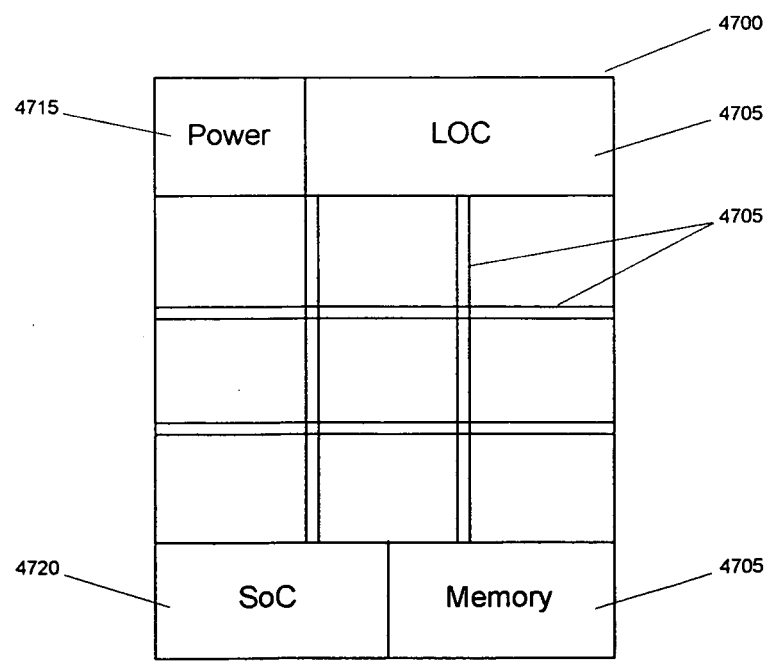
FIG. 47 is a schematic diagram showing an integrated iMD with analytical and diagnostic components on the periphery of a therapeutic core.

Though the iMD is configured with an analytical module, a diagnostic module and therapeutic module(s) in the preferred embodiment, in other embodiments, the three modules are integrated into a single device with configurations that emphasize a specific purpose, such as diagnosis or therapy. In FIG. 47, a two dimensional drawing of a top view of an integrated iMD (4700) is shown. In this figure, the analytical components of the SoC (4720) and digital memory (4725) are at the bottom and the LoC (4705) and power supply (4715) are at the top. The core therapeutic components are in the center of the drawing, with the microfluidic conduits (4710) representing the main part of the device. In this integrated configuration, the LoC maximizes its efficiency. The therapeutic components are still able transform their structures to perform novel procedures to solve complex optimization problems. In a sense, the therapeutic module is intact in this configuration, with supplemental diagnostic and analytical components added on the periphery of the device. Given the therapeutic emphasis of this embodiment of the iMD, the integrated device is useful for specific types of therapy. However, the increased efficiency of this model sacrifices multi-functionality of the modular iMD architecture.

Figure 48:
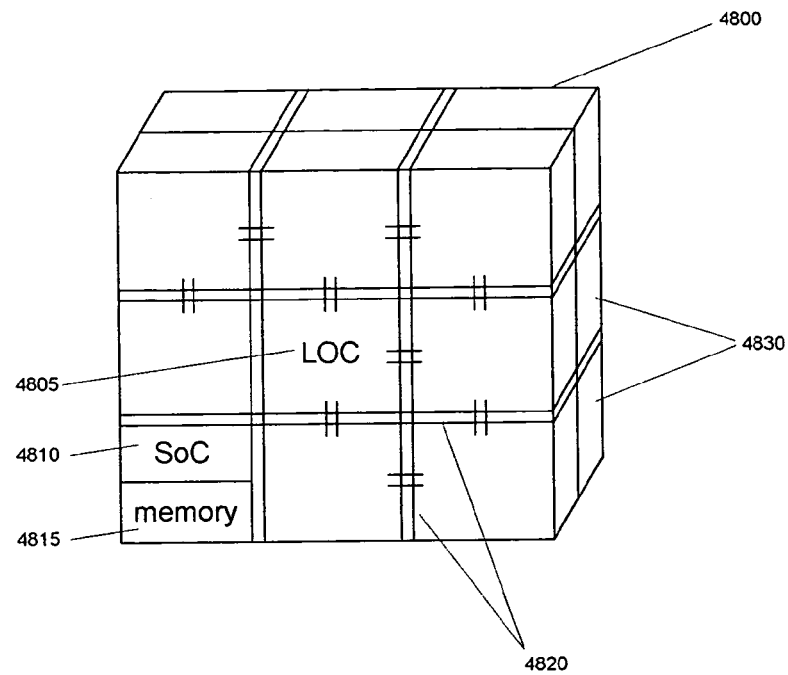
FIG. 48 is a schematic diagram showing an integrated 3D iMD with analytical and diagnostic components consolidated into the therapeutic components.

In another embodiment of an integrated iMD configuration, FIG. 48 shows a three dimensional representation of a diagnostic-centric device (4800), with the LOC (4805) in the center of one set of components on one side, while the SoC (4810) and digital memory (4815) are located in one compartment. The microfluidic conduit network is shown at 4820 connecting the compartments. In this configuration, the iMD is able to analyze and test samples in the LOC in the center, while the outer layers of the front façade and the compartments of the rear façade (4830) conduct therapeutic functions of combining chemicals and biologicals for treating pathologies. In this configuration, the iMD maximizes therapeutic functionality while also maintaining some diagnostic functionality by accessing the LOC. Although the analytical functionality is restricted relative to the modular configuration, the iMD is able to access external computer resources as well as other iMDs in a network. Like the modular iMD model, the therapeutic compartments are also transformational. However, the degree of transformation may be restricted in this configuration, much like an FPGA semiconductor that is only able to shift from one ASIC position to another pre-assigned ASIC position. While not containing the multifunctionality of the modular configuration, this configuration is able to solve many medical problems.

Figure 49:
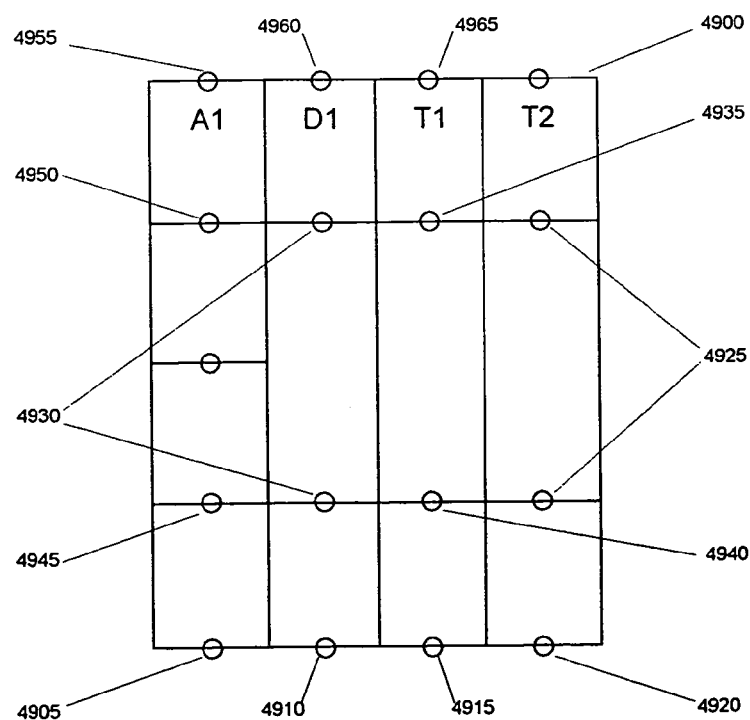
FIG. 49 is a drawing of a sensor grid in an iMD that tracks functions.
Figure 50:
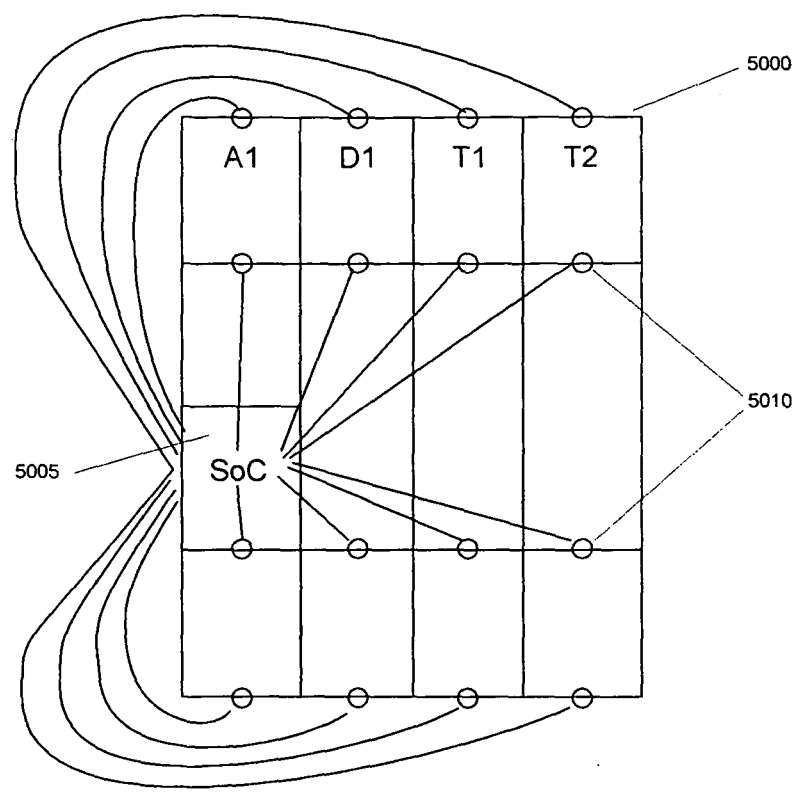
FIG. 50 is a schematic diagram showing a sensor network in an iMD that uses an SoC for self-diagnostics.

FIG. 49 shows the sensor grid in a modular iMD. The sensors (4905-4950) are organized at positions connecting the compartments of the iMD. The sensors are controlled by the SoC in the analytical module. FIG. 50 shows the operation of the sensors (5010) in the sensor network with the SoC (5005). The sensor network uses the SoC for self-diagnostics. The sensors are in constant contact with the SoC. When the sensors are activated by a function of a compartment, the SoC registers the action. Conversely, when the SoC controller activates a specific set of functions, the sensors are activated and the actuators in specific compartments are activated to perform a specific function.

Figure 51:
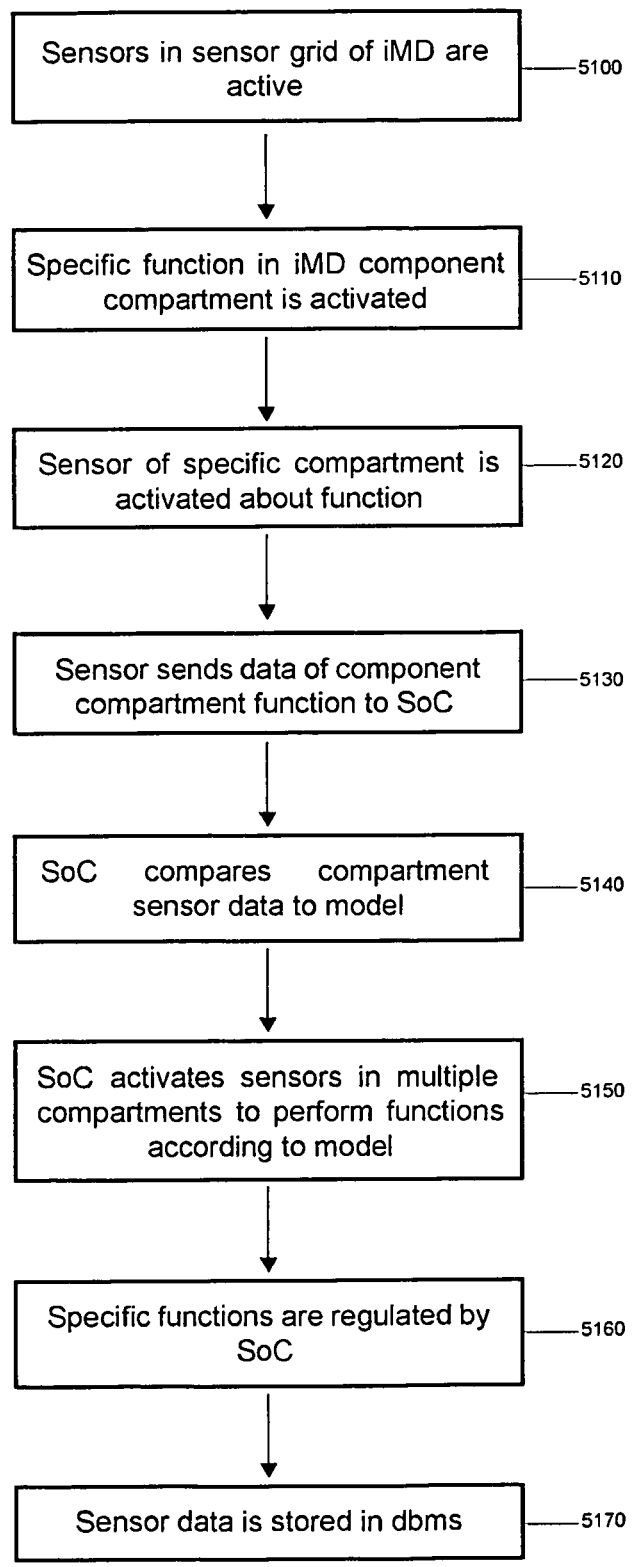
FIG. 51 is a flow chart describing the process of operation of a sensor network in an iMD.

FIG. 51 describes the process of the operation of a sensor network in an iMD. After first activating the sensors in the iMD sensor grid (5100), a specific function in an iMD component compartment is activated (5110) and the sensor of a specific compartment is activated about a specific function (5120). The sensor then sends data about the component compartment function to the SoC (5130) and the SoC compares the sensor data to a model (5140). The SoC activates sensors in multiple compartments to perform functions according to the model (5150). The specific functions are regulated by the SoC (5160) and the sensor data is stored in the dbms (5170).

Figure 52:
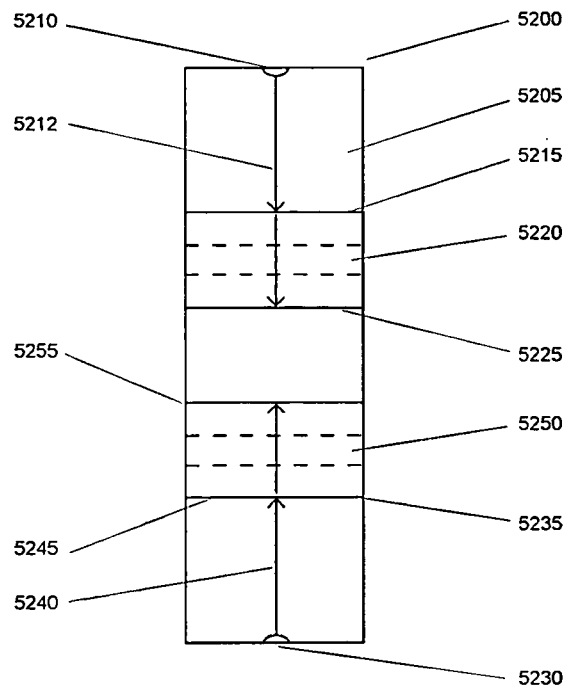
FIG. 52 is a schematic diagram showing a side view of a therapeutic module in which the size and configuration of a compartment is reconfigured with pressure plates.

FIG. 52 is a drawing of a side view of a therapeutic module in which the size and configuration of a compartment is reconfigured with pressure plates. While the reconfiguration of the diagnostic and therapeutic modules occurs as referenced above, in one embodiment, the pressure plates (5215 and 5245) are used to push on two sides. The pressure is applied by using pumps (5210 and 5230) at both ends of the compartment. The pressure plate at the top moves from position 5215 to positions at 5220 and finally to position at 5225, while the pressure plate at the bottom moves from position 5235 to positions at 5250 and finally to position at 5255. The pressure plates are driven by arms 5212 and 5240. This model allows an easy way to rapidly modify the configuration of a chamber. It is also useful to use pressure to combine and mix chemicals in a chamber.

Figure 53:
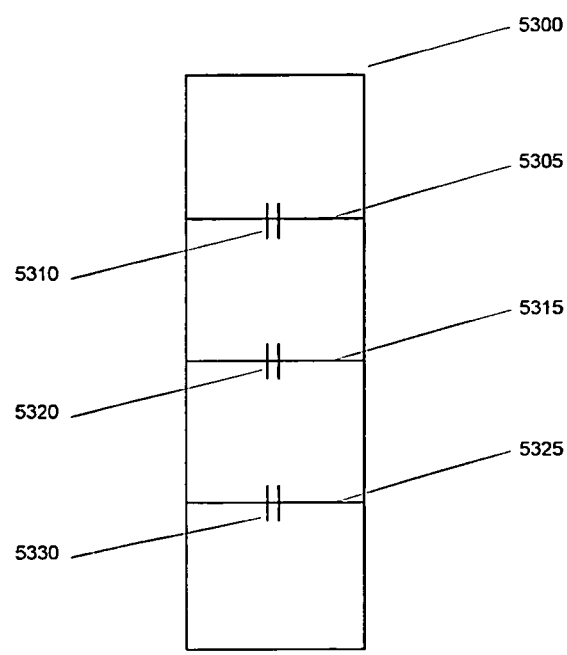
FIG. 53 is a drawing of a side view of a therapeutic module in which drugs are measured and regulated in each chamber.

The problem of measuring and regulating the content, size and flow of chemicals is significant. It is imperative to precisely measure and regulate chemicals and biologicals in the iMD modules. In FIG. 53, a therapeutic module side view is shown in which drugs are precisely measured by calculating the size of the chamber and the flow rate of the drugs. Specific pre-measured chemicals are released and stored in adjacent chambers. In the course of a therapy, the chemicals or biologicals are precisely measured, combined in a specific chamber, and expelled to perform a therapeutic function. The chambers are then evacuated and cleaned by rinsing with a neutral fluid and the chambers are reused or reconfigured upon demand.

Figure 54:
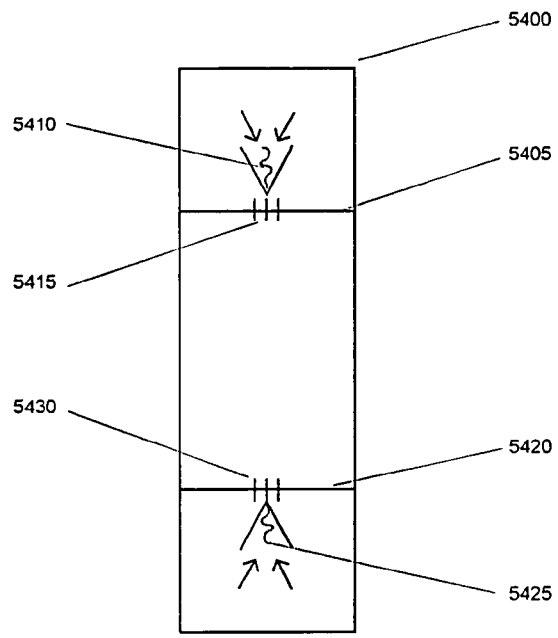
FIG. 54 is a drawing of a side view of a therapeutic module showing an adjustable corkscrew to open and close the valves at specific compartments.

In another embodiment of the valve connections between the chambers, FIG. 54 shows a side view of a therapeutic module in which the valves have adjustable corkscrew devices (5410 and 5425) to open and close the valves (5415 and 5430) at the junctions between the compartments. The advantage of this approach is that the corkscrews can be precisely modulated to allow specific flows of chemicals or biologicals into the chambers. This approach is particularly useful in allowing chemicals or biologicals on the periphery storage compartments of the module to flow into the central chamber of the device for mixing of a combination of therapies before final application to a medical pathology.

Figure 55:
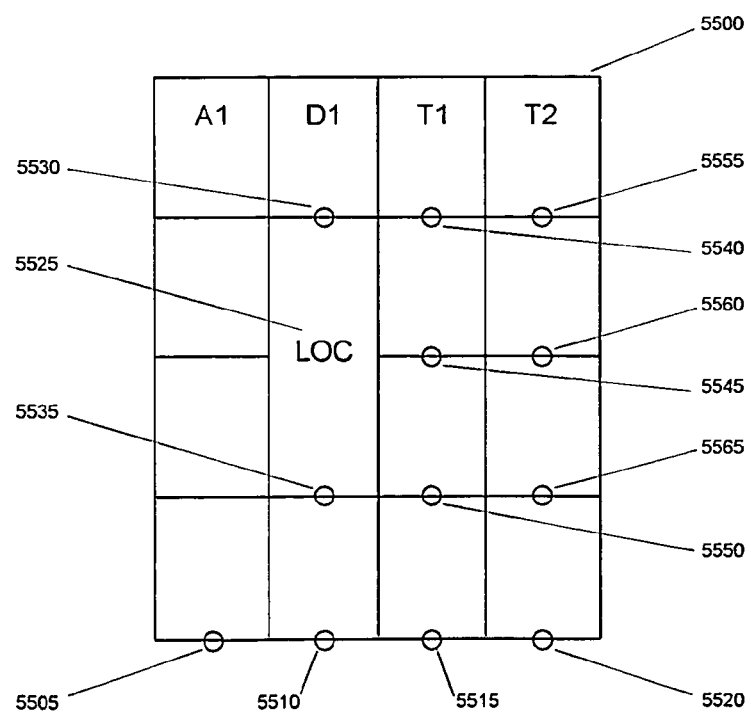
FIG. 55 is a schematic diagram showing the stop light functionality to control network activities between chambers.

In order to organize the functions in the modules of the iMD, the system uses a network control process similar to a set of stop lights. In FIG. 55, the stop light functionality is used to control the network activities between the chambers. The analytical (5505), diagnostic (5510) and therapeutic (5515 and 5520) modules are shown. The sensors (5530 to 5565) are located at the junctions between chambers and are activated and controlled by the SoC in the analytical module.

Figure 56:
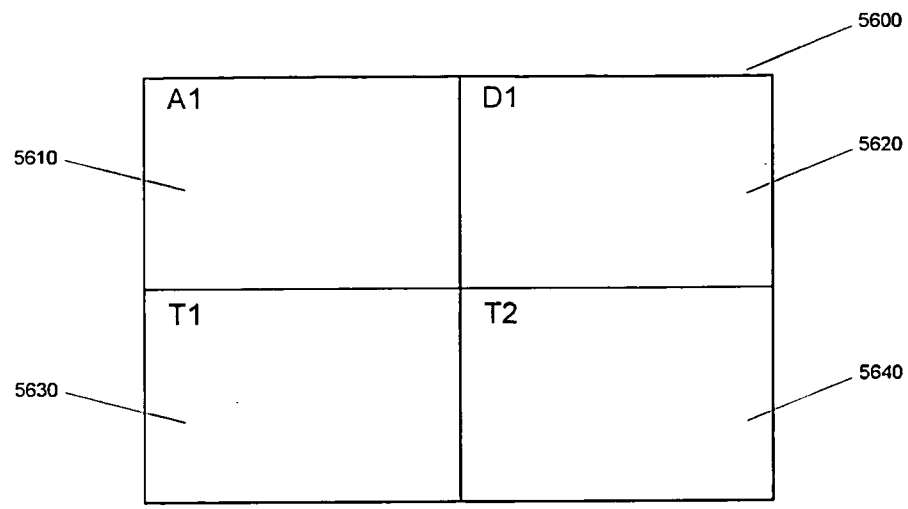
FIG. 56 is a diagram of iMD modules configured in adjacent tiles on a plane.

FIG. 56 shows the iMD modules configured in adjacent tiles on a plane. In this embodiment, rather than layering the iMD modules, they are set out on a flat surface. This configuration has an advantage of allowing the architecture of the iMD to be very flat for specific applications. In the drawing, the analytical module (5610), the diagnostic module (5620) and the therapeutic modules are configured in adjacent tiles.

Figure 57:
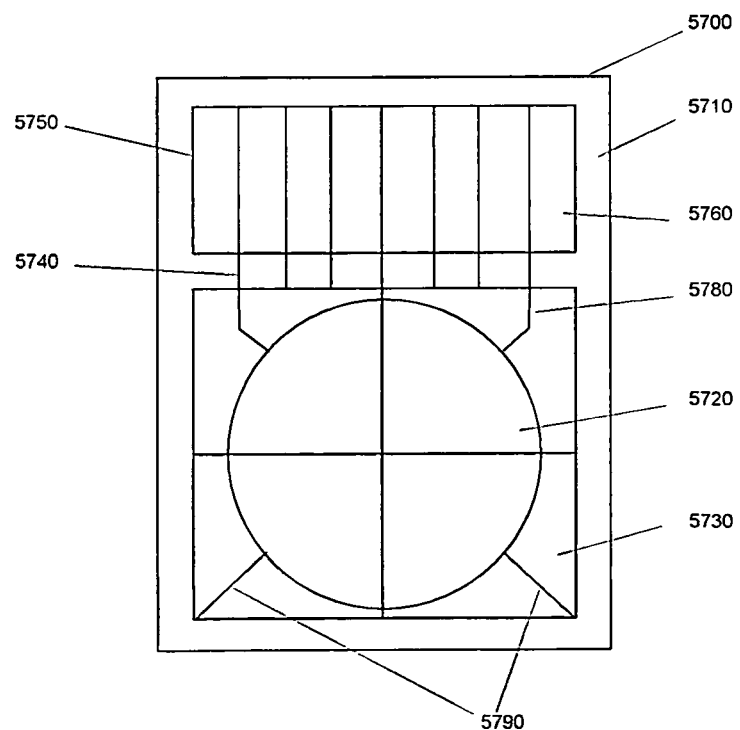
FIG. 57 is a schematic diagram of a disk based LOC on one layer of a diagnostic module.
Figure 58:
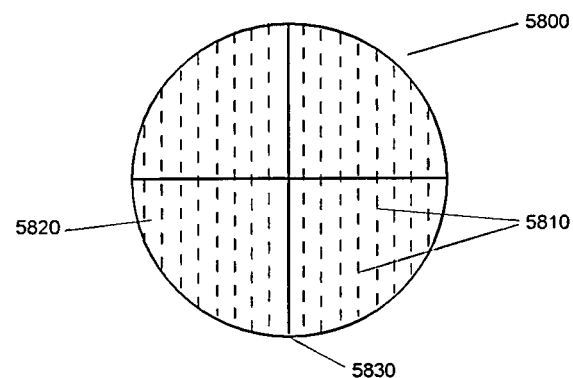
FIG. 58 is a diagram of a top view of a testing disk with wells.

FIG. 57 shows a top view of a disk based lab on a chip (LOC) on one layer of a diagnostic module. This component is also called a lab on a disk. The disk (5720) is shown as a circle in the center of a square shaped circuit (5730). The electrical connections (5790) are connected to the control mechanisms. The chemicals, analytes and biologicals are stored in the compartments (5760) in the grid at the top (5750). Neutral fluid is also stored in the storage grid in order to clean the surface of the disk for later experiments. The microfluidic conduits connect the storage facility to the disk (5740 and 5780. The disk itself has wells (5810) positioned on its surface for testing various chemicals and biologicals (e.g., cells, DNA, RNA and proteins), as shown in FIG. 58. The disk is shown split into four equal quadrants. The disk based model for testing of chemicals and biologicals is useful for positioning in a layer of the diagnostic module. In one embodiment, each quadrant of the disk is used separately to test different components. For example, in one quadrant, whole cells are tested, while in another, proteins are tested. This multifunctional utility of the disk increases functionality of the disk based model. The disk size will vary in different embodiments, thereby allowing a range of surface area access to testing. A large disk will test a larger range of samples, thereby accelerating the testing process. In one embodiment of the system, the disk on a biochip is constructed using complementary metal oxide semiconductor (CMOS) fabrication technology.

Figure 59:
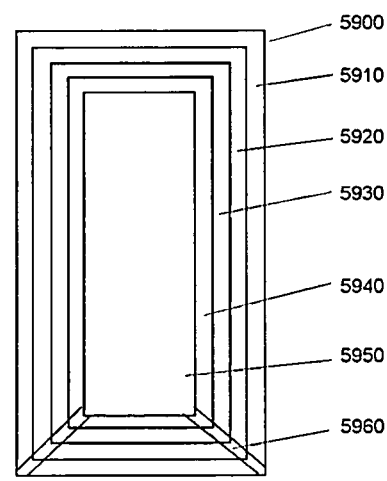
FIG. 59 is a diagram of a top view of a multi-layer diagnostic module.

FIG. 59 shows a top view of a multi-layer diagnostic module. Each layer is shown (5910 to 5950) as a tiered nest. The conduits in the corners (5960) allow transference of fluids to different levels. This model is similar to a multi-tier building structure.

Figure 60:
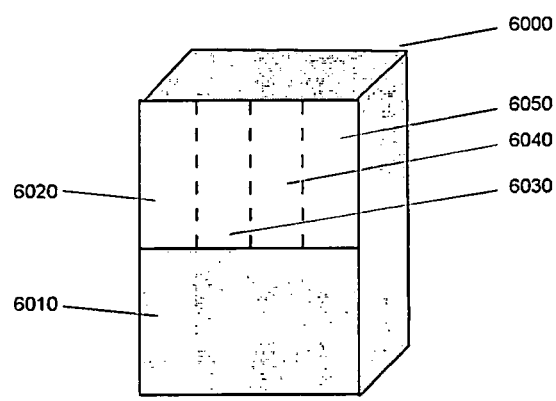
FIG. 60 is a diagram of a cut out view of an iMD showing the external packaging.

FIG. 60 shows a cut out view of an iMD (6000) showing the external packaging. The individual modules (analytical, diagnostic and therapeutic) are shown (6020 to 6050) on the interior. The external packaging (6010) may be made from different ceramics, plastics, metals or some combination of advanced materials.

I claim:

1. An apparatus for managing microfluidic components in a medical device, comprising:
   at least three modules connected by microfluidic channels, including a diagnostic module, an analytical module and a therapeutic module;
   each module capable of receiving and/or analyzing fluids;
   an integrated circuit configured to control the modules;
   each module capable of processing or transmitting electrical signals;
   wherein the modules conduct differentiated functions of analysis, diagnostics or therapeutics;
   wherein the integrated circuit controls the functions of the diagnostic, analytical and therapeutic modules;
   wherein the diagnostic, analytical and therapeutic modules are connected with electrical interconnects;
   wherein the diagnostic module comprises a lab-on-a-chip (LOC) for testing of biological samples and transfers the test results to the analytical module;
   wherein the analytical module includes a system on a chip (SoC) to conduct modeling functions and store and access data in a database management system;
   wherein the therapeutic module comprises a set of compartments for managing chemicals and/or biologicals; and
   wherein the therapeutic module receives modeling data from the analytical model and configures the compartments to combine chemicals and/or biologicals to solve a pathological problem.

2. An apparatus for managing electrical components in a medical device, comprising:
   at least two layers of medical component modules in a multi-layer device;
   a diagnostic module that includes a lab-on-a-chip (LOC);
   an analytical module that includes a system on a chip (SoC) to conduct modeling functions and store and access data in a database management system;
   a therapeutic module that includes a set of compartments for organizing chemicals and biologicals;
   a diagnostic module, an analytical module and a therapeutic module configured in layers;
   an integrated circuit configured to control the modules;
   electrical interconnects configured to connect adjacent layers;
   wherein each layer uses electrical interconnects to connect components within each layer;
   wherein the integrated circuit sends and receives electrical signals between the diagnostic module and/or therapeutic module;
   wherein electrical signals are transmitted through the interconnects from one layer of the multilayer device to other layers; and
   wherein at least one layer of the multilayer medical device performs computational tasks and sends electrical signals to at least one other layer.

3. An apparatus for managing microfluidic components in a medical device, comprising:
   a diagnostic module, including a lab-on-a-chip (LOC) component, configured to process and test cell, DNA, RNA and/or protein samples;
   a therapeutic module including compartments to process chemicals and/or biologicals, wherein the compartments are connected by microfluidic channels;
   at least two layers of medical component modules configured in a multi-layer device;
   each microfluidic layer capable of receiving and processing fluids;

wherein the at least two microfluidic layers are connected by microfluidic channels;

wherein the microfluidic layers are configured to receive and process chemical and/or biological fluids;

wherein an integrated circuit is configured to control the combination of fluids in at least one chamber of one compartment of the therapeutic module; and wherein the fluids that are output from the therapeutic module apply a therapy related to a pathology processed in the diagnostic module wherein the integrated circuit is configured to apply the combined fluids are applied to at least one patient tissue site.

4. The apparatus of claim 1, wherein:
the analytical modeling functions include DNA and/or RNA testing.

5. The apparatus of claim 1, wherein:
the analytical modeling functions include protein testing.

6. The apparatus of claim 1, wherein:
the analytical modeling functions include whole cell testing.

7. The apparatus of claim 3, wherein:
the microfluidic components on layers of the therapeutics module include micro-valves, micro-tubes and micro-gates to control the flow of fluids.

8. The apparatus of claim 1, wherein:
the analytical module includes a system on a chip (SoC) and software to perform modeling.

9. The apparatus of claim 1, wherein:
biological samples comprise inputs for the diagnostic module; and
the biological samples consist of cell, DNA, RNA and/or protein constituent parts.

10. The apparatus of claim 1, wherein:
the analytical module models unique patient pathology; and
the unique pathology consists of identifying a combination of mutations.

11. The apparatus of claim 1, wherein:
the therapeutic module applies combined fluids to patient tissue.

12. The apparatus of claim 2, wherein:
the diagnostic module sends electrical signals to the analytical module and/or the therapeutic module.

13. The apparatus of claim 2, wherein:
the analytical module sends electrical signals to the diagnostic module and/or the therapeutic module.

14. The apparatus of claim 2, wherein:
the therapeutic module sends electrical signals to the diagnostic module and/or the analytical module.

15. The apparatus of claim 3, wherein:
the microfluidic channels connect fluidic chambers of the device.

16. The apparatus of claim 3, wherein:
at least two chambers of the microfluidic module are configured in layers.

17. The apparatus of claim 3, wherein:
at least two chambers of the therapeutics module are configured to send and receive fluids by using the micro fluidic channels.

18. The apparatus of claim 1, wherein:
the integrated circuit that controls the functional modules is an ASIC, FPGA or SoC.

* * * * *